United States Patent [19]
Loring et al.

[11] Patent Number: 5,981,175
[45] Date of Patent: Nov. 9, 1999

[54] METHODS FOR PRODUCING RECOMBINANT MAMMALIAN CELLS HARBORING A YEAST ARTIFICIAL CHROMOSOME

[75] Inventors: Jeanne F. Loring, Foster City; Theodore Choi, Burlingame; Robert M. Kay, San Francisco, all of Calif.

[73] Assignee: Genpharm Internation, Inc., Mountain View, Calif.

[21] Appl. No.: 08/187,161

[22] Filed: Jan. 25, 1994

Related U.S. Application Data

[63] Continuation-in-part of application No. 08/079,444, Jun. 18, 1993, abandoned, which is a continuation-in-part of application No. 08/001,493, Jan. 7, 1993, abandoned.

[51] Int. Cl.[6] ........................................................ C12Q 1/68
[52] U.S. Cl. ............................................. 435/6; 435/172.3
[58] Field of Search ........................... 435/6, 172.3, 172, 435/2; 800/2

[56] References Cited

U.S. PATENT DOCUMENTS

| | | | |
|---|---|---|---|
| 4,634,665 | 1/1987 | Axel et al. | 435/69.1 |
| 4,736,866 | 4/1988 | Leder et al. | 800/2 |
| 4,873,191 | 10/1989 | Wagner et al. | 435/172.3 |
| 5,175,383 | 12/1992 | Leder et al. | 800/2 |
| 5,175,384 | 12/1992 | Krimpenfort et al. | 435/172.3 |
| 5,175,385 | 12/1992 | Wagner et al. | 800/2 |
| 5,266,489 | 11/1993 | Rey-Senelonge et al. | 435/320.1 |
| 5,283,185 | 2/1994 | Epand et al. | 435/172.3 |

FOREIGN PATENT DOCUMENTS

WO/93/05165   3/1993   WIPO.

OTHER PUBLICATIONS

Ho et al., *J. Vir. Methods*, vol. 32, 1991, pp. 79–88.
Davies et al., *Nuc. Acids Res.*, vol. 20, 1992, pp. 2693–2698.
Yoshikai et al., *Gene*, vol. 87, 1990, pp. 257–263.
Strojek et al., Genetic Engineering: Principles and Methods, vol. 10, Ed. Jane K. Setlow, pp. 221–246.
Su, Z.Z. et al., Anticancer Research, 12:297–304, 1992.
Hadlaczky, G. et al., Proc. Natl. Acad. Sci., 88:(18)8106–8110, 1991.
Choi, T.K. et al., Nat. Genet., 4:(2)P117–23, Jun. 1993.
Palmiter et al., Ann. Rev. Genet., 20:465–499, (1986).
Schedl et al., Nucleic Acids Research 20:12:3073–3077, (1992).
Gnirke et al., The EMBO Journal, 10:7:1629–1634 (1991).
D'Urso et al., Genomics 7:531–534 (1990).
Felgner et al., Proc. Natl. Acad. Sci. USA 84:7413–7417 (1987).
Gossler et al., Proc. Natl. Acad. Sci. USA 83:9065–9069 (1986).
Strauss et al., The EMBO Journal 11:2:417–422 (1992).
Quon et al., Nature 352:239–241 (1991).
Holt et al., Neuron 4:203–214 (1990).
Sandhu et al., J. Biol. Chem. 266:21331–21334 (1991).
Meade et al., Bio/Technology 8:443–446 (1990).
Kotula, et al., Bio/Technology 9:1386 (1991).
Bradley, et al., Bio/Technology 10:534–539 (1992).

*Primary Examiner*—James Ketter
*Attorney, Agent, or Firm*—Cooley Godward LLP

[57] ABSTRACT

The present invention provides methods and compositions for transferring large transgene polynucleotides and unlinked selectable marker polynucleotides into eukaryotic cells by a novel method designated co-lipofection. The methods and compositions of the invention are used to produce novel transgenic non-human animals harboring large transgenes, such as a transgene comprising a human APP gene or human immunoglobulin gene.

11 Claims, 9 Drawing Sheets

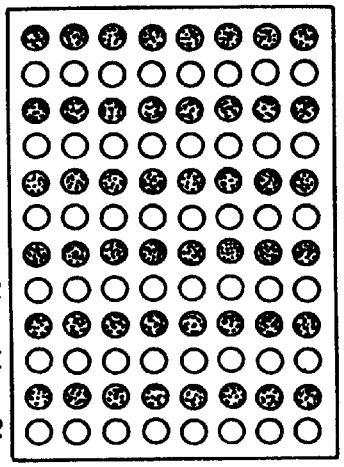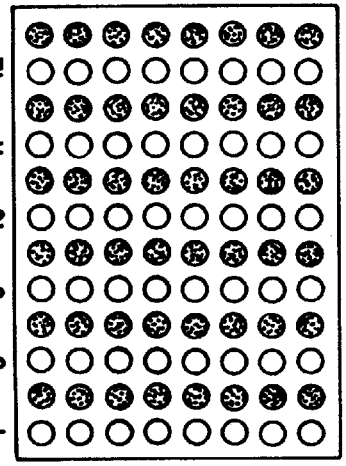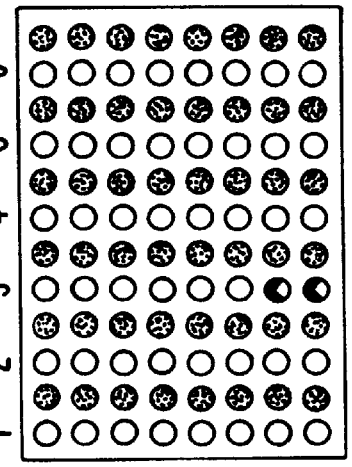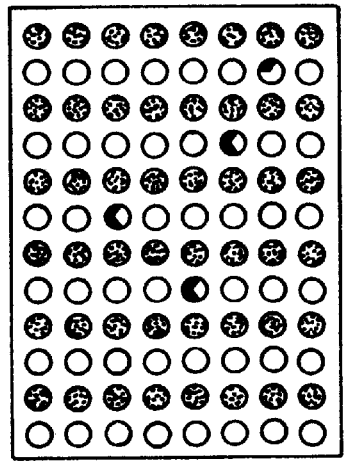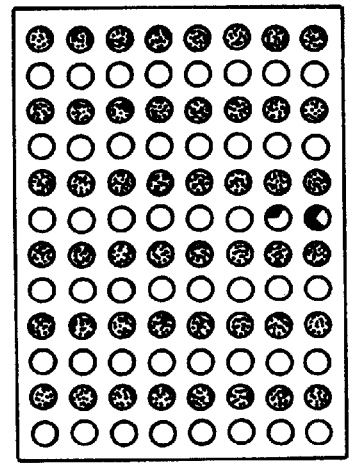
FIG. 4.

METHODS FOR PRODUCING RECOMBINANT MAMMALIAN CELLS HARBORING A YEAST ARTIFICIAL CHROMOSOME

This application is a continuation-in-part of Ser. No. 08/079,444, filed Jun. 18, 1993, now abandoned, which is a continuation-in-part of Ser. No. 08/001,493, filed Jan. 7, 1993, now abandoned.

TECHNICAL FIELD

The invention relates to transgenic non-human animals capable of expressing xenogenic polypeptides, transgenes used to produce such transgenic animals, transgenes capable of expressing xenogenic polypeptides, yeast artificial chromosomes comprising a polynucleotide sequence encoding a human protein such as a human immunoglobulin or amyloid precursor protein (APP), methods and transgenes for transferring large polynucleotide sequences into cells, and methods for co-lipofection of discontinuous polynucleotide sequences into cells.

BACKGROUND OF THE INVENTION

Transferring exogenous genetic material into cells is the basis for modern molecular biology. The continuing development of novel methods for improving the efficiency, specificity, and/or size limitations of the transfer process has broadened the scope of research and product development by enabling the production of polynucleotide clones and recombinant organisms that previously were impractical or impossible to construct. Calcium phosphate precipitation, electroporation, lipofection, ballistic transfer, DEAE-dextran transfection, microinjection, and viral-based transfer methods, among others, have been described for introducing foreign DNA fragments into mammalian cells.

The art also has developed yeast artificial chromosome ("YAC") cloning vectors which are capable of propagating large (50 to more than 1000 kilobases) cloned inserts (U.S. Pat. No. 4,889,806) of xenogenic DNA. YAC clone libraries have been used to identify, map, and propagate large fragments of mammalian genomic DNA. YAC cloning is especially useful for isolating intact genes, particularly large genes having exons spanning several tens of kilobases or more, and genes having distal regulatory elements located tens of kilobases or more upstream or downstream from the exonic sequences. YAC cloning is particularly advantageous for isolating large complex gene loci, such as unrearranged immunoglobulin gene loci, and genes which have been inexactly mapped to an approximate chromosomal region (e.g., a Huntington's chorea gene). YAC cloning is also well-suited for making vectors for performing targeted homologous recombination in mammalian cells, since YACs allow the cloning of large contiguous sequences useful as recombinogenic homology regions in homologous targeting vectors. Moreover, YACs afford a system for doing targeted homologous recombination in a yeast host cell to create novel, large transgenes (e.g., large minigenes, tandem gene arrays, etc.) in YAC constructs which could then be transferred to mammalian host cells.

Unfortunately, manipulation of large polynucleotides is problematic. Large polynucleotides are susceptible to breakage by shearing forces and form highly viscous solutions even at relatively dilute concentrations, making in vitro manipulation exceedingly difficult. For these reasons, and others, it is desirable to reduce the amount of manipulation that YAC clones and other large DNA fragments are subjected to in the process of constructing large transgene constructs or homologous recombination constructs.

More problematic is the fact that the transfer of large, intact polynucleotides into mammalian cells is typically inefficient or provides a restriction on the size of the polynucleotide transferred. For example, Schedl et al. (1992) *Nucleic Acids Res.* 20: 3073, describe transferring a 35 kilobase YAC clone into the mouse genome by pronuclear injection of murine embryos; however, the shear forces produced in the injection micropipette will almost certainly preclude the efficient transfer of significantly larger YAC clones in an intact form. Many large genes likely could not be transferred efficiently into mammalian cells by current microinjection methods.

Spheroplast fusion has been used to introduce YAC DNA into fibroblasts, embryonal carcinoma cells, and CHO cells (Pachnie et al. (1990) *Proc. Natl. Acad. Sci.* (*U.S.A.*) 87: 5109; Payan et al. (1990) *Mol. Cell. Biol.* 10: 4163; Chirke et al. (1991) *EMBO J.* 10: 1629; Davies et al. (1992) *Nucleic Acids Res.* 20: 2693). Alternative transfection methods such as calcium phosphate precipitation and lipofection have been used to transfer YAC DNA into mammalian cells (Eticciri et al. (1991) *Proc. Natl. Acad. Sci.* (*U.S.A.*) 88: 2179; Strauss W and Jaenisch R (1992) *EMBO J.* 11: 417).

Thus, there exists a need in the art for an efficient method for transferring large segments of DNA, such as large YAC clones, into mammalian cells, such as embryonic stem cells for making transgenic animals, with a minimum of manipulation and cloning procedures. In particular, it would be highly advantageous if it were possible to isolate a large cloned mammalian genomic fragment from a YAC library, either linked to YAC yeast sequences or purified away from YAC yeast sequences, and transfer it intact into a mammalian host cell (e.g., an ES cell) with a second polynucleotide sequence (e.g., a selectable marker such as a $neo^r$ expression cassette) without additional cloning or manipulation (e.g., ligation of the sequences to each other). Such a method would allow the efficient construction of transgenic cells, transgenic animals, and homologously targeted cells and animals. These transgenic/homologously targeted cells and animals could provide useful models of, for example, human genetic diseases such as Huntington's chorea and Alzheimer's disease, among others.

Alzheimer's Disease

At present there is no known therapy for the various forms of Alzheimer's disease (AD). However, there are several disease states for which effective treatment is available and which give rise to progressive intellectual deterioration closely resembling the dementia associated with Alzheimer's disease.

Alzheimer's disease is a progressive disease known generally as senile dementia. Broadly speaking the disease falls into two categories, namely late onset and early onset. Late onset, which occurs in old age (65+ years), may be caused by the natural atrophy of the brain occurring at a faster rate and to a more severe degree than normal. Early onset Alzheimer's disease is much more infrequent but shows a pathologically identical dementia with brain atrophy which develops well before the senile period, i.e., between the ages of 35 and 60 years. There is evidence that one form of this type of Alzheimer's disease is inherited and is therefore known as familial Alzheimer's disease (FAD).

In both types of Alzheimer's disease the pathology is the same but the abnormalities tend to be more severe and more widespread in cases beginning at an earlier age. The disease is characterized by four types of lesions in the brain, these are: amyloid plaques around neurons (senile plaques), amyloid deposits around cerebral blood vessels, neurofibrillary tangles inside neurons, and neuronal cell death. Senile plaques are areas of disorganized neuropil up to 150 μm across with extracellular amyloid deposits at the center. Cerebrovascular amyloid deposits are amyloid material surrounding cerebral blood vessels. Neurofibrillary tangles are intracellular deposits of amyloid protein consisting of two filaments twisted about each other in pairs.

The major protein subunit, amyloid β protein, is found in amyloid filaments of both the neurofibrillary tangle and the senile plaque and is a highly aggregating small polypeptide of approximate relative molecular mass 4,000.

This protein is a cleavage product of a much larger precursor protein called amyloid precursor protein (APP).

The APP gene is known to be located on human chromosome 21. A locus segregating with familial Alzheimer's disease has been mapped to chromosome 21 (St. George Hyslop et al (1987) *Science* 235: 885) close to the APP gene.

Recombinants between the APP gene and the AD locus have been previously reported (Schellenberg et al. (1988) *Science* 241: 1507; Schellenberg et al. (1991) *Am. J. Hum. Genetics* 48: 563; Schellenberg et al. (1991) *Am. J. Hum. Genetics* 49: 511, incorporated herein by reference). The development of experimental models of Alzheimer's disease that can be used to define further the underlying biochemical events involved in AD pathogenesis would be highly desirable. Such models could presumably be employed, in one application, to screen for agents that alter the degenerative course of Alzheimer's disease. For example, a model system of Alzheimer's disease could be used to screen for environmental factors that induce or accelerate the pathogenesis of AD. In contradistinction, an experimental model could be used to screen for agents that inhibit, prevent, or reverse the progression of AD. Presumably, such models could be employed to develop pharmaceuticals that are effective in preventing, arresting, or reversing AD.

Unfortunately, only humans and aged non-human primates develop any of the pathological features of AD; the expense and difficulty of using primates and the length of time required for developing the AD pathology makes extensive research on such animals prohibitive. Rodents do not develop AD, even at an extreme age. It has been reported that the injection of β-amyloid protein (βAP) or cytotoxic βAP fragments into rodent brain results in cell loss and induces an antigenic marker for neurofibrillary tangle components (Kowall et al. (1991) *Proc. Natl. Acad. Sci. (U.S.A.)* 88: 7247). Mice which carry an extra copy of the APP gene as a result of partial trisomy of chromosome 16 die before birth (Coyle et al. (1988) *Trends in Neurosci.* 11: 390). Since the cloning of the APP gene, there have been several attempts to produce a mouse model for AD using transgenes that include all or part of the APP gene, unfortunately much of the work remains unpublished since the mice were nonviable or failed to show AD-like pathology; two published reports were retracted because of irregularities in reported results (Marx J *Science* 255: 1200).

Thus, there is also a need in the art for transgenic nonhuman animals harboring an intact human APP gene, either a wild-type allele, a disease-associated allele, or a combination of these, or a mutated rodent (e.g., murine) allele which comprises sequence modifications which correspond to a human APP sequence. Cell strains and cell lines (e.g., astroglial cells) derived from such transgenic animals would also find wide application in the art as experimental models for developing AD therapeutics.

Nonhuman Transgenic Animals Expressing Human Immunoglobulin

Making human monoclonal antibodies that bind predetermined antigens is difficult, requiring a source of viable lymphocytes from a human that has been immunized with an antigen of choice and which has made a substantial humoral immune response to the immunogen. In particular, humans generally are incapable of making a substantial antibody response to a challenge with a human (self) antigen; unfortunately, many such human antigens are promising targets for therapeutic strategies involving human monoclonal antibodies. One approach to making human antibodies that are specifically reactive with predetermined human antigens involves producing transgenic mice harboring unrearranged human immunoglobulin transgenes and having functionally disrupted endogenous immunoglobulin gene(s) (Lonberg and Kay, WO 92/03918; Kucherlapati and Jakobovits, WO 91/10741). However, efficiently transferring large DNA segments, such as those spanning significant portions of a human light or heavy chain immunoglobulin gene locus, presents a potential obstacle and/or reduces the efficiency of the process of generating the transgenic animals.

Based on the foregoing, it is clear that a need exists for nonhuman cells and nonhuman animals harboring one or more large, intact transgenes, particularly a human APP gene or a human immunoglobulin transgene(s). Thus, it is an object of the invention herein to provide methods and compositions for transferring large transgenes and large homologous recombination constructs, usually cloned as YACs, into mammalian cells, especially into embryonic stem cells. It is also an object of the invention to provide transgenic nonhuman cells and transgenic nonhuman animals harboring one or more APP transgenes of the invention.

The references discussed herein are provided solely for their disclosure prior to the filing date of the present application. Nothing herein is to be construed as an admission that the inventors are not entitled to antedate such disclosure by virtue of prior invention. All citations are incorporated herein by reference.

SUMMARY OF THE INVENTION

In accordance with the foregoing objects, in one aspect of the invention methods for transferring large transgenes and large homologous targeting constructs, typically propagated as YACs and preferably spanning at least one complete transcriptional complex, into mammalian cells, such as ES cells, are provided. In one aspect, the methods provide for transferring the large transgenes and large homologous targeting constructs by a lipofection method, such as co-lipofection, wherein a second unlinked polynucleotide is transferred into the mammalian cells along with the large transgene and/or large homologous targeting construct. Preferably, the second polynucleotide confers a selectable phenotype (e.g., resistance to G418 selection) to cells which have taken up and integrated the polynucleotide sequence(s). Usually, the large transgene or homologous targeting construct is transferred with yeast-derived YAC sequences in polynucleotide linkage, but yeast-derived YAC sequences may be removed by restriction enzyme digestion and separation (e.g, pulsed gel electrophoresis). The large transgene(s) and/or homologous targeting construct(s) are generally mixed with the unlinked second polynucleotide (e.g., a neo$^R$ expression cassette to confer a selectable phenotype) and contacted with a cationic lipid (e.g., DOGS, DOTMA, DOTAP) to form cationic lipid-DNA complexes which are contacted with mammalian cells (e.g., ES cells) in conditions suitable for uptake of the DNA into the cells (e.g., culture medium, physiological phosphate-buffered saline, serum-free ES medium). Generally, cells harboring the large transgene or large homologous targeting construct concomitantly harbor at least one copy of the second polynucleotide, so that selection for cells harboring the second polynucleotide have a significant probability of also harboring at least one copy of the large transgene or large homologous targeting construct, generally as an integrated or homologously recombined segment of an endogenous chromosomal locus. Hence selection for the second polynucleotide (e.g., $neo^R$ expression cassette) generally also selects cells harboring the large transgene or large homologous targeting construct without requiring cumbersome polynucleotide linkage (i.e., ligation) of the large transgene or large homologous targeting construct to the second polynucleotide prior to lipofection. According to the co-lipofection methods of the invention, large segments of xenogenic DNA are rapidly and efficiently transferred into mammalian cells (e.g., murine ES cells) without requiring linkage of a selectable marker gene and subsequent cloning.

The invention also provides mammalian cells, preferably ES cells, harboring at least one copy of integrated or homologously recombined large xenogenic (preferably heterologous) mammalian genomic DNA sequences linked to yeast-derived YAC sequences. Preferably, the large xenogenic (preferably heterologous) mammalian genomic DNA sequences comprise a complete structural gene, more preferably a complete transcriptional unit, and in one embodiment a complete human APP gene. Typically, the resultant transgenic mammalian cells also comprise at least one integrated copy of the unlinked second polynucleotide (e.g., the selectable marker), which is usually nonhomologously integrated into at least one chromosomal locus, sometimes at a chromosomal locus distinct from that at which the large transgene(s) or large homologous targeting construct(s) has been incorporated. During the transfection process and shortly thereafter, novel mammalian cells, such as ES cells, comprising large foreign DNA sequences, an unlinked selectable marker gene, and a suitable cationic lipid are formed, such novel mammalian cells are one aspect of the present invention.

The invention also provides transgenic nonhuman animals comprising a genome having at least one copy of integrated or homologously recombined large xenogenic (preferably heterologous) mammalian genomic DNA sequences linked to yeast-derived YAC sequences. Preferably, the large xenogenic (preferably heterologous) mammalian genomic DNA sequences comprise a complete structural gene, more preferably a complete transcriptional unit, and in one embodiment a complete human APP gene. Typically, the resultant transgenic nonhuman mammal also comprises a genome having at least one integrated copy of the unlinked second polynucleotide (e.g., the selectable marker), which is usually nonhomologously integrated into at least one chromosomal locus, sometimes at a chromosomal locus/loci distinct from that at which the large transgene(s) or large homologous targeting construct(s) has/have been incorporated. Preferably, the large transgene and/or large homologous targeting construct which has been incorporated into a chromosomal locus (or loci) of the nonhuman animal is expressed, more preferably is expressed similarly to the naturally-occurring homolog gene in the non-human animal species (e.g., in a similar tissue-specific pattern and/or developmental pattern).

The invention also provides compositions for co-lipofection: transgenesis compositions and homologous targeting compositions for transferring xenogenic, typically heterologous, large (i.e., 50 kb or more) polynucleotides into mammalian cells, such as ES cells for making transgenic nonhuman animals harboring at least one copy of at least one integrated large foreign transgene and/or harboring at least one homologously targeted construct in its genome. A transgenesis composition comprises: (1) at least one large transgene species, (2) at least one unlinked second polynucleotide species (such as an expression cassette containing the selectable marker gene $neo^R$), and (3) at least one species of suitable cationic lipid. A homologous targeting composition comprises: (1) at least one large homologous targeting construct species, (2) at least one unlinked second polynucleotide species (such as an expression cassette containing the selectable marker gene $neo^R$), and (3) at least one species of suitable cationic lipid. Preferably the large transgene or large homologous targeting construct spans an entire transcriptional unit. One preferred embodiment of a co-lipofection composition is a composition comprising: (1) a human APP gene sequence (or a modified murine or rat APP gene having a non-naturally occurring sequence corresponding to a human APP sequence) linked to yeast-derived YAC sequences, (2) an expression cassette encoding a selectable marker, and (3) a suitable cationic lipid. Another preferred embodiment of a co-lipofection composition is a composition comprising: (1) a human unrearranged immunoglobulin gene sequence (heavy or light chain gene sequence comprising at least two V gene complete segment, at least one complete D segment (if heavy chain gene), at least one complete J segment, and at least one constant region gene) linked to yeast-derived YAC sequences, (2) an expression cassette encoding a selectable marker, and (3) a suitable cationic lipid.

In one aspect of the invention, multiple species of unlinked polynucleotide sequences are co-lipofected into murine embryonic stem cells and/or other mammalian cells, wherein at least one species of the unlinked polynucleotide sequences comprises a selectable marker gene which confers a selectable phenotype to cells which have incorporated it. The resultant cells are selected for the presence of the selectable marker; such selected cells have a significant probability of comprising at least one integrated copy of the other species of polynucleotide sequence(s) introduced into the cells.

BRIEF DESCRIPTION OF THE FIGURES

FIG. 4: PCR analysis of ES clones co-lipofected with the human APP transgene.

DEFINITIONS

Figure 1:
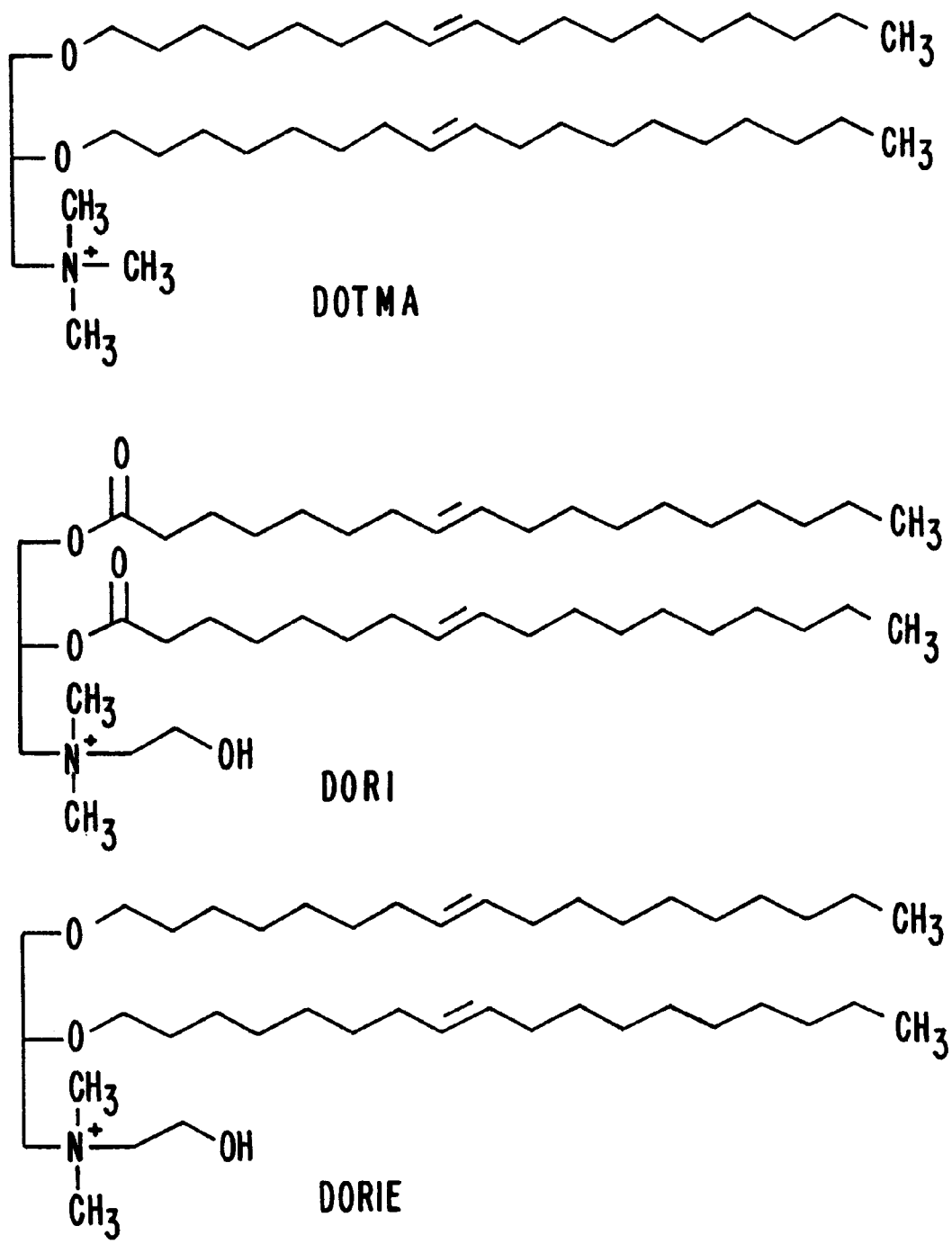
FIG. 1: Chemical structures of representative cationic lipids for forming co-lipofection complexes of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The terms "substantially corresponds to", "substantially homologous", or "substantial identity" as used herein denotes a characteristic of a nucleic acid sequence, wherein a nucleic acid sequence has at least 70 percent sequence identity as compared to a reference sequence, typically at least 85 percent sequence identity, and preferably at least 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least 30 nucleotides long, and preferably at least 50 to 100 nucleotides long. "Substantially complementary" as used herein refers to a sequence that is complementary to a sequence that substantially corresponds to a reference sequence.

Specific hybridization is defined herein as the formation of hybrids between a targeting transgene sequence (e.g., a polynucleotide of the invention which may include substitutions, deletion, and/or additions) and a specific target DNA sequence (e.g., a human APP gene sequence or human immunoglobulin gene sequence), wherein a labeled targeting transgene sequence preferentially hybridizes to the target such that, for example, a single band corresponding to a restriction fragment of a gene can be identified on a Southern blot of DNA prepared from cells using said labeled targeting transgene sequence as a probe. It is evident that optimal hybridization conditions will vary depending upon the sequence composition and length(s) of the targeting transgene(s) and endogenous target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "cognate" as used herein refers to a gene sequence that is evolutionarily and functionally related between species. For example but not limitation, in the human genome, the human immunoglobulin heavy chain gene locus is the cognate gene to the mouse immunoglobulin heavy chain gene locus, since the sequences and structures of these two genes indicate that they are highly homologous and both genes encode a protein which functions to bind antigens specifically.

As used herein, the term "xenogenic" is defined in relation to a recipient mammalian host cell or nonhuman animal and means that an amino acid sequence or polynucleotide sequence is not encoded by or present in, respectively, the naturally-occurring genome of the recipient mammalian host cell or nonhuman animal. Xenogenic DNA sequences are foreign DNA sequences; for example, human APP genes or immunoglobulin genes are xenogenic with respect to murine ES cells; also, for illustration, a human cystic fibrosis-associated CFTR allele is xenogenic with respect to a human cell line that is homozygous for wild-type (normal) CFTR alleles. Thus, a cloned murine nucleic acid sequence that has been mutated (e.g., by site directed mutagenesis) is xenogenic with respect to the murine genome from which the sequence was originally derived, if the mutated sequence does not naturally occur in the murine genome.

As used herein, a "heterologous gene" or "heterologous polynucleotide sequence" is defined in relation to the transgenic nonhuman organism producing such a gene product. A heterologous polypeptide, also referred to as a xenogeneic polypeptide, is defined as a polypeptide having an amino acid sequence or an encoding DNA sequence corresponding to that of a cognate gene found in an organism not consisting of the transgenic nonhuman animal. Thus, a transgenic mouse harboring a human APP gene can be described as harboring a heterologous APP gene. A transgenic mouse harboring a human immunoglobulin gene can be described as harboring a heterologous immunoglobulin gene. A transgene containing various gene segments encoding a heterologous protein sequence may be readily identified, e.g. by hybridization or DNA sequencing, as being from a species of organism other than the transgenic animal. For example, expression of human APP amino acid sequences may be detected in the transgenic nonhuman animals of the invention with antibodies specific for human APP epitopes encoded by human AP gene segments. A cognate heterologous gene refers to a corresponding gene from another species; thus, if murine APP is the reference, human APP is a cognate heterologous gene (as is porcine, ovine, or rat APP, along with AP genes from other species).

As used herein, the term "targeting construct" refers to a polynucleotide which comprises: (1) at least one homology region having a sequence that is substantially identical to or substantially complementary to a sequence present in a host cell endogenous gene locus, and (2) a targeting region which becomes integrated into a host cell endogenous gene locus by homologous recombination between a targeting construct homology region and said endogenous gene locus sequence.

If the targeting construct is a "hit-and-run" or "in-and-out" type construct (Valancius and Smithies (1991) *Mol. Cell. Biol.* 11: 1402; Donehower et al. (1992) *Nature* 356: 215; (1991) *J. NIH Res.* 3: 59; Hasty et al. (1991) *Nature* 350; 243, which are incorporated herein by reference), the targeting region is only transiently incorporated into the endogenous gene locus and is eliminated from the host genome by selection. A targeting region may comprise a sequence that is substantially homologous to an endogenous gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion) of a targeting construct having a sequence that substantially corresponds to, or is substantially complementary to, a predetermined endogenous gene sequence, which can include sequences flanking said gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The terms "homology clamp" and "homology region" are interchangeable as used herein, and the alternative terminology is offered for clarity, in view of the inconsistent usage of similar terms in the art. A homology clamp does not necessarily connote formation of a base-paired hybrid structure with an endogenous sequence. Endogenous gene sequences that substantially correspond to, or are substantially complementary to, a transgene homology region are referred to herein as "cross-over target sequences" or "endogenous target sequences."

As used herein, the term "minigene" or "minilocus" refers to a heterologous gene construct wherein one or more nonessential segments of a gene are deleted with respect to the naturally-occurring gene. Typically, deleted segments are intronic sequences of at least about 100 basepairs to several kilobases, and may span up to several tens of kilobases or more. Isolation and manipulation of large (i.e., greater than about 50 kilobases) targeting constructs is frequently difficult and may reduce the efficiency of transferring the targeting construct into a host cell. Thus, it is frequently desirable to reduce the size of a targeting construct by deleting one or more nonessential portions of the gene. Typically, intronic sequences that do not encompass essential regulatory elements may be deleted. For example, a human immunoglobulin heavy chain minigene may comprise a deletion of an intronic segment between the J gene segments and the $\mu$ constant region exons of the human heavy chain immunoglobulin gene locus. Frequently, if convenient restriction sites bound a nonessential intronic sequence of a cloned gene sequence, a deletion of the intronic sequence may be produced by: (1) digesting the cloned DNA with the appropriate restriction enzymes, (2) separating the restriction fragments (e.g., by electrophoresis), (3) isolating the restriction fragments encompassing the essential exons and regulatory elements, and (4) ligating the isolated restriction fragments to form a minigene wherein the exons are in the same linear order as is present in the germline copy of the naturally-occurring gene.

Alternate methods for producing a minigene will be apparent to those of skill in the art (e.g., ligation of partial genomic clones which encompass essential exons but which lack portions of intronic sequence). Most typically, the gene segments comprising a minigene will be arranged in the same linear order as is present in the germline gene, however, this will not always be the case. Some desired regulatory elements (e.g., enhancers, silencers) may be relatively position-insensitive, so that the regulatory element will function correctly even if positioned differently in a minigene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a minigene. Similarly, some genes may have exons which are alternatively spliced at the RNA level, and thus a minigene may have fewer exons and/or exons in a different linear order than the corresponding germline gene and still encode a functional gene product. A cDNA encoding a gene product may also be used to construct a minigene. However, since it is generally desirable that the heterologous minigene be expressed similarly to the cognate naturally-occurring nonhuman gene, transcription of a cDNA minigene typically is driven by a linked gene promoter and enhancer from the naturally-occurring gene.

As used herein, the term "large transgene" or "large homologous targeting construct" generally refers to polynucleotides that are larger than 50 kb, usually larger than 100 kb, frequently larger than 260 kb, occasionally as large as 500 kb, and sometimes as large as 1000 kb or larger.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

As used herein, "linked" means in polynucleotide linkage (i.e., phosphodiester linkage). "Unlinked" means not linked to another polynucleotide sequence; hence, two sequences are unlinked if each sequence has a free 5' terminus and a free 3' terminus.

DETAILED DESCRIPTION OF THE INVENTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., lipofection protocols). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference).

Oligonucleotides can be synthesized on an Applied Bio Systems oligonucleotide synthesizer according to specifications provided by the manufacturer.

It has often been observed that cDNA-based transgenes are poorly expressed or inappropriately regulated. Genomic DNA-based transgenes (i.e., constructed from cloned genomic DNA sequences) which substantially retain the content and organization of the naturally-occurring gene locus are more likely to be correctly expressed, but are limited in size by the cloning capacity of bacteriophage and plasmid/cosmid vectors. The yeast artificial chromosome (YAC) is a recently developed cloning vehicle with a capacity of approximately 2 megabases (Mb) (Burke et al. (1987) *Science* 236: 806). The ability to reproducibly and efficiently introduce YACs into transgenic mice can significantly surpass current transgene size limits.

In general, the invention is based on the unexpected finding that large (i.e., greater than about 50 kb) cloned polynucleotides can be efficiently transferred into mammalian cells, such as ES cells, and are incorporated into at least one chromosomal location and stably replicated as a segment of a chromosome. Further, it was found that large cloned polynucleotides comprising a complete transcriptional unit can be transferred into mammalian cells (e.g., ES cells), incorporated into a chromosomal location, and transcribed to produce a detectable concentration of RNA transcripts of the structural gene sequences. It was also found that unrearranged immunoglobulin genes cloned in YACs can be introduced into ES cells and developed to form a transgenic animal in which productive VDJ rearrangement occurs, and expression of immunoglobulin chains also occurs. It has also been found that large transgenes can be cloned in YACs and, after isolation from the host yeast cells, efficiently transferred into mammalian cells (e.g., ES cells) without prior separation of the desired transgene sequences from yeast-derived YAC sequences, and that the presence of such yeast-derived YAC sequences can be non-interfering (i.e., compatible with efficient transgene integration and transcription of a transgene transcriptional unit). Unexpectedly, it also has been found that large transgenes, with or without linked yeast-derived YAC sequences, can be efficiently co-transfected into mammalian cells (e.g., ES cells) with unlinked polynucleotides containing a selectable marker, such as, for example, a neo$^R$ expression cassette; and that selection for cells harboring the selectable marker gene and expressing the selectable marker are are highly likely to also harbor the large transgene species which has been co-lipofected, thus allowing efficient selection for large transgene DNA sequences without requiring prior ligation (and cloning) of a selectable marker gene. The finding that large DNA segments, such as YAC clones, can be efficiently co-lipofected with a selectable marker gene permits, for the first time, the construction of transgenic mammalian cells and transgenic nonhuman animals harboring large xenogenic DNA segments that are typically difficult to manipulate. Thus, large polynucleotides, typically 50 to 100 kb in size, frequently more than 250 kb in size, occasionally more than about 500 kb, and sometimes 1000 kb or larger, may be efficiently introduced into mammalian cells. The mammalian cells may be ES cells, such as murine ES cells (e.g., the AB-1 line), so that the resultant transgenic cells can be injected into blastocysts to generate transgenic nonhuman animals, such as transgenic mice or transgenic rats, harboring large DNA transgenes, which are preferably expressed in the nonhuman transgenic animals. The present methods may also be carried out with somatic cells, such as epithelial cells (e.g., keratinocytes), endothelial cells, hematopoietic cells, and myocytes, for example.

Embryonic Stem Cells

If embryonic stem (ES) cells are used as the transgene recipients, it is possible to develop a transgenic animal harboring the targeted gene(s) which comprise the integrated targeting transgene(s). Briefly, this technology involves the introduction of a gene, by nonhomologous integration or homologous recombination, in a pluripotent cell line (e.g., a murine ES cell line) that is capable of differentiating into germ cell tissue.

A large transgene can be nonhomologously integrated into a chromosomal location of the host genome. Alternatively, a homologous targeting construct (which may comprise a transgene) that contains at least one altered copy of a portion of a germline gene or a xenogenic cognate gene (including heterologous genes) can be introduced into the genome of embryonic stem cells. In a portion of the cells, the introduced DNA is either nonhomologously integrated into a chromosomal location or homologously recombines with the endogenous (i.e., naturally occurring) copy of the mouse gene, replacing it with the altered construct. Cells containing the newly engineered genetic sequence(s) are injected into a host mouse blastocyst, which is reimplanted into a recipient female. Some of these embryos develop into chimeric mice that possess a population of germ cells partially derived from the mutant cell line. Therefore, by breeding the chimeric mice it is possible to obtain a new line of mice containing the introduced genetic lesion (reviewed by Capecchi et al. (1989) *Science* 244: 1288, incorporated herein by reference).

For homologous targeting constructs, targeting efficiency generally increases with the length of the targeting transgene portion (i.e., homology region) that is substantially complementary to a reference sequence present in the target DNA (i.e., crossover target sequence). In general, targeting efficiency is optimized with the use of isogenic DNA homology regions, although it is recognized that the presence of recombinases in certain ES cell clones may reduce the degree of sequence identity required for efficient recombination.

The invention also provides transgenes which encode a gene product that is xenogenic (e.g., heterologous) to a nonhuman host species. Such transgenes typically comprise a structural gene sequence expression cassette, wherein a linked promoter and, preferably, an enhancer drive expression of structural sequences encoding a xenogenic (e.g., heterologous protein). For example, the invention provides transgenes which comprise a mammalian enhancer and at least one human APP promoter linked to structural sequences that encode a human APP protein. Transgenic mice harboring such transgenes express human APP mRNA (s). Preferably, the polynucleotide sequence encoding the xenogenic (e.g., heterologous) protein is operably linked to cis-acting transcriptional regulatory regions (e.g., promoter, enhancer) so that a heterologous protein is expressed in a manner similar to the expression of the cognate endogenous gene in the naturally-occurring nonhuman animal. Thus, it is generally preferable to operably link a transgene structural encoding sequence to transcriptional regulatory elements which naturally occur in or near the cognate endogenous gene. However, transgenes encoding heterologous proteins may be targeted by employing a homologous gene targeting construct targeted adjacent to the endogenous transcriptional regulatory sequences, so that the operable linkage of a regulatory sequence occurs upon integration of the transgene into a targeted endogenous chromosomal location of the ES cell.

Selectable Marker Genes

A selectable marker gene expression cassette typically comprises a promoter which is operational in the targeted host cell (e.g., ES cell) linked to a structural sequence that encodes a protein or polypeptide that confers a selectable phenotype on the targeted host cell, and a polyadenylation signal. A promoter included in an expression cassette may be constitutive, cell type-specific, stage-specific, and/or modulatable (e.g., by hormones such as glucocorticoids; MMTV promoter), but is expressed prior to and/or during selection. An expression cassette can optionally include one or more enhancers, typically linked upstream of the promoter and within about 3–10 kilobases. However, when the selectable marker is contained in a homologous targeting construct, homologous recombination at the targeted endogenous site(s) can be chosen to place the selectable marker structural sequence downstream of a functional endogenous promoter, and it may be possible for the targeting construct replacement region to comprise only a structural sequence encoding the selectable marker, and rely upon an endogenous promoter to drive transcription (Doetschman et al. (1988) *Proc. Natl. Acad. Sci.* (*U.S.A.*) 85: 8583, incorporated herein by reference). Similarly, an endogenous enhancer located near a targeted endogenous site may be relied on to enhance transcription of selectable marker gene sequences in enhancerless constructs. Preferred expression cassettes of the invention encode and express a selectable drug resistance marker and/or a HSV thymidine kinase enzyme. Suitable drug resistance genes include, for example: gpt (xanthine-guanine phosphoribosyltransferase), which can be selected for with mycophenolic acid; neo (neomycin phosphotransferase), which can be selected for with G418, hygromycin, or puromycin; and DFHR (dihydrofolate reductase), which can be selected for with methotrexate (Mulligan and Berg (1981) *Proc. Natl. Acad. Sci.* (*U.S.A.*) 78: 2072; Southern and Berg (1982) *J. Mol. Appl. Genet.* 1: 327; which are incorporated herein by reference). Other suitable selectable markers will be apparent to those in the art.

Selection for correctly co-lipofected recombinants will generally employ at least positive selection, wherein a selectable marker gene expression cassette encodes and expresses a functional protein (e.g., neo or gpt) that confers a selectable phenotype to targeted cells harboring the endogenously integrated expression cassette, so that, by addition of a selection agent (e.g., G418, puromycin, or mycophenolic acid) such targeted cells have a growth or survival advantage over cells which do not have an integrated expression cassette. Further guidance regarding selectable marker genes is available in several publications, including Smith and Berg (1984) *Cold Spring Harbor Symp. Quant. Biol.* 49: 171; Sedivy and Sharp (1989) *Proc. Natl. Acad. Sci.* (*U.S.A.*) 86: 227; Thomas and Capecchi (1987) op.cit., which are incorporated herein by reference.

Large Xenogenic Polynucleotides

Large polynucleotides are usually cloned in YAC vectors. For example, human genomic DNA libraries in YAC cloning vectors can be screened (e.g., by PCR or labeled polynucleotide probe hybridization) to isolate YAC clones spanning complete genes of interest (e.g., a human APP gene, a human immunoglobulin heavy chain locus or light chain locus), or significant portions of such genes which comprise a complete transcriptional unit. Methods for making YAC libraries, isolating desired YAC clones, and purifying YAC DNA are described in the art (U.S. Pat. No. 4,889,806; Burke et al. (1987) *Science* 236: 806; Murry et al. (1986) *Cell* 45: 529, incorporated herein by reference).

Once a desired YAC clone is isolated, and preferably deproteinized, yeast-derived YAC sequences may optionally be completely or partially removed by digestion with one or more restriction enzymes which cut outside the desired cloned large transgene sequence; yeast-derived sequences are separated from the cloned insert sequences by, for example, pulsed gel electrophoresis. Preferably, a complete unrearranged YAC clone is used as a large transgene or large homologous targeting construct in the methods of the invention.

In one aspect, preferred YAC clones are those which completely or partially span structural gene sequences selected from the group consisting of: human APP gene, human immunoglobulin heavy chain locus, human immunoglobulin light chain locus, human al-antitrypsin gene, human Duchenne muscular dystrophy gene, human Huntington's chorea-associated loci, and other large structural genes, preferably human genes.

Preferred YAC cloning vectors are: a modified pYAC3 vector (Burke et al. (1987) op.cit., incorporated herein by reference), pYACneo (Traver et al. (1989) *Proc. Natl. Acad. Sci.* (*U.S.A.*) 86: 5898, incorporated herein by reference), and pCGS966 (Smith et al. (1990) *Proc. Natl. Acad. Sci.* (*U.S.A.*) 87: 8242, incorporated herein by reference).

Cationic Lipids

Lipofection, and various variations of its basic methodology, have been described previously in the art (U.S. Pat. Nos. 5,049,386; 4,946,787; and 4,897,355) and lipofection reagents are now sold commercially (e.g., "Transfectam" and "Lipofectin").

Cationic and neutral lipids that are suitable for efficient lipofection of DNA have been described in the art. Lipofection may be accomplished by forming lipid complexes with DNA made according to Felgner (WO91/17424, incorporated herein by reference) and/or cationic lipidization (WO91/16024; incorporated herein by reference). Various lipofection protocols described in the art may be adapted for co-lipofection according to the invention; for example but not limitation, general lipofection protocols are described in the following references which are incorporated herein:

Behr et al. (1989) *Proc. Natl. Acad. Sci. (U.S.A.)* 86: 6982; Demeneix et al. (1991) *Int. J. Dev. Biol.* 35: 481; Loeffler et al. (1990) *J. Neurochem.* 54; 1812; Bennett et al. (1992) *Mol. Pharmacol.* 41: 1023; Bertling et al. (1991) *Biotechnol. Appl. Biochem.* 13: 390; Felgner et al. (1987) *Proc. Natl. Acad. Sci. (U.S.A.)* 84: 7413; Felgner and Ringold (1989) *Nature* 337: 387; Gareis et al. (1991) *Cell. Mol. Biol.* 37: 191; Jarnagin et al. (1992) *Nucleic Acids Res.* 20: 4205; Jiao et al. (1992) *Exp. Neurol.* 115: 400; Lim et al. (1991) *Circulation* 83: 2007; Malone et al. (1989) *Proc. Natl. Acad. Sci. (U.S.A.)* 86: 6077; Powell et al. (1992) *Eur. J. Vasc. Surg.* 6: 130; Strauss and Jaenisch (1992) *EMBO J.* 11: 417; and Leventis and Silvius (1990) *Biochim. Biophys. Acta* 1023: 124.

Newer polycationic lipospermines compounds exhibit broad cell ranges (Behr et al., (1989) *op.cit.*) and DNA is coated by these compounds. In addition, a combination of neutral and cationic lipid has been shown to be highly efficient at transfection of animal cells and showed a broad spectrum of effectiveness in a variety of cell lines (Rose et al., (1991) *BioTechniques* 10:520)

A lipofection complex (or a cationic lipidized DNA complex) is defined as the product made by mixing a suitable cationic lipid composition with one or more polynucleotide species, such as a large transgene and a selectable marker gene expression cassette. Such a co-lipofection complex is characterized by an interaction between the polynucleotides and lipid components that results in the formation of a co- lipofection complex that, when contacted with mammalian cells under suitable conditions (e.g., buffered saline or ES cell medium with or without serum, 20–45° C.), results in incorporation of the polynucleotides into the mammalian cells; preferably the mammalian cells are ES cells, such as murine ES cells.

Various suitable cationic lipids may be used, either alone or in combination with one or more other cationic lipid species or neutral lipid species. Generally, suitable cationic lipids comprise a positively charged head group (one or more charges) and a covalently linked fatty acid tail. A suitable cationic lipid composition is "Transfectam" (ProMega, Madison, Wis.) comprising the cationic lipid-polyamine dioctadecylamidoglycyl spermidine (DOGS). DOTMA is a preferred lipid known as N-(2,3-di(9-(Z)-octadecenyloxy))-prop-1-N,N,N- trimethylammonium chloride. DNA-DOTMA complexes made essentially from DOTMA and DNA. Other examples of suitable cationic lipids are: dioleoylphosphatidylethanolamine (PtdEtn, DOPE), dioctadecylamidoglycyl, N-trimethylammonium chloride, N-trimethylammonium methylsulfate, DORI and DORI-ether (DORIE). DORI is N-[1-(2,3-dioleoyl)propyl3-N,N-dimethyl-N-hydroxyethylammonium acetate and DORIE is N-[1-(2,3-dioleyloxy)propyl]-N,N-dimethyl-N-hydroxyethylammonium acetate. DOTAP is N-[1-(2,3-dioleoyloxy)propyl]-N,N,N-trimethylammonium methyl sulfate; this lipid has ester rather than ether linkages and can be metabolized by cells.

Optionally, one or more co-lipids may be combined with a suitable cationic lipid. An optional co-lipid is to be understood as a structure capable of producing a stable DNA-lipid complex, alone with DNA, or in combination with other lipid components and DNA, and is preferably neutral, although it can alternatively be positively or negatively charged. Examples of optional co-lipids are phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, dioleoylphosphatidylcholine (DOPC), dipalmitoyl-phosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoylphosphatidylethanolamine (POPE) and dioleoylphosphatidylethanolamine 4-(N-maleimidomethyl)-cyclohexane-1-carboxylate (DOPE-mal). Additional non-phosphorous containing lipids are, e.g.,stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like.

Generally, to form a lipofection complex, the polynucleotide(s) is/are combined according to the teachings in the art and herein with a suitable cationic lipid, in the presence or absence of one or more co-lipids, at about pH 7.4–7.8 and 20–30° C. When more than one species of polynucleotide are combined in a lipofection complex it may be referred to herein as a co-lipofection complex. A co-lipofection complex generally comprises a large polynucleotide (a transgene or homologously targeting construct) and a selectable marker gene expression cassette. The co-lipofection complex is administered to a cell culture, preferably murine ES cells, under lipofection conditions as described in the art and herein.

General Methods

A preferred method of the invention is to transfer a substantially intact YAC clone comprising a large heterologous transgene into a pluripotent stem cell line which can be used to generate transgenic nonhuman animals following injection into a host blastocyst. A particularly preferred embodiment of the invention is a human APP gene targeting construct co-lipofected with an unlinked positive (e.g., neo) selection expression cassette. The human APP transgene is transferred into mouse ES cells (e.g., by co-lipofection with neo) under conditions suitable for the continued viability of the co-lipofected ES cells. The lipofected ES cells are cultured under selective conditions for positive selection (e.g., a selective concentration of G418). Selected cells are then verified as having the correctly targeted transgene recombination by PCR analysis according to standard PCR or Southern blotting methods known in the art (U.S. Pat. No. 4,683,202; Erlich et al., (1991) *Science* 252: 1643, which are incorporated herein by reference).

Correctly targeted ES cells are then transferred into suitable blastocyst hosts for generation of chimeric transgenic animals according to methods known in the art (Capecchi, M. (1989) TIG 5:70; Capecchi, M. (1989) *Science* 244:1288, incorporated herein by reference). Several studies have already used PCR to successfully identify the desired transfected cell lines (Zimmer and Gruss (1989) *Nature* 338: 150; Mouellic et al. (1990) *Proc. Natl. Acad. Sci. (U.S.A.)* 87: 4712; Shesely et al. (1991) *Proc. Natl. Acad. Sci. USA* 88: 4294, which are incorporated herein by reference). This approach is very effective when the number of cells receiving exogenous targeting transgene(s) is high (i.e., with electroporation or lipofection) and the treated cell populations are allowed to expand (Capecchi, M. (1989) *op.cit.*, incorporated herein by reference).

For making transgenic non-human animals (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073–1085 (1990)) essentially as described (Robertson, E. J. (1987) in *Teratocarcinomas and Embryonic Stem Cells: A Practical Approach.* E. J. Robertson, ed. (Oxford: IRL Press), p. 71–112) may be used for homologous gene targeting. Other suitable ES lines include, but are not limited to, the E14 line (Hooper et al. (1987) *Nature* 326: 292–295), the D3 line (Doetschman et al. (1985) *J. Embryol. Exp. Morph.* 87: 27–45), and the CCE line (Robertson et al. (1986) *Nature* 323: 445–448). Rat, hamster, bovine, and porcine ES cell lines are also available in the art for producing non-murine transgenic non-human animals bearing a human APP gene sequence. The success of generating a mouse line from ES cells bearing a large transgene or specifically targeted genetic alteration depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having the large transgene(s)/ homologous targeting constructs and are backcrossed and screened for the presence of the transgene(s) and/or YAC sequences by PCR or Southern blot analysis on tail biopsy DNA of offspring so as to identify transgenic mice heterozygous for the transgene(s)/homologous targeting constructs. By performing the appropriate crosses, it is possible to produce a transgenic nonhuman animal homozygous for multiple large transgenes/homologous recombination constructs, and optionally also for a transgene encoding a different heterologous protein. Such transgenic animals are satisfactory experimental models for various diseases linked to the transferred transgene(s).

For performing certain types of studies, transgenic rats harboring and expressing a human APP sequence may be preferred.

EXPERIMENTAL EXAMPLES

EXAMPLE 1

Materials and Transfection Calibration

Pilot experiments to determine toxicity levels, optimum DNA:lipid ratios, etc. were performed with] (2 kb PGKneo cassette in pUC) and with PYPNN (a modified pYACneo vector containing a PGKneo cassette in place of the SV40-neo cassette in the acentric arm.

The YAC used in these calibration experiments was an 85 kb human IgH gene fragment cloned into a modified pYAC-neo vector (EcoRI->NotI cloning site alteration). The YAC was thus 100 kb in length including the vector arms.

DOTMA (Lipofectin, BRL, Bethesda, Md.) and DOGS (Transfectam, ProMega, Madison, Wis.) were tested as cationic lipids. FIG. 1 shows chemical structures of representative cationic lipids which can be used to form co-lipofection complexes. ES cell toxicity curves were performed for each. Toxic effects could be seen with DOTMA at the 30 $\mu$g/ml level. DOGS showed no toxic effects at the 60 $\mu$g/ml level.

Optimal DNA:lipid ratios were determined for both lipids, using pGKneo as reporter. Optima for DOTMA and DOGS were at 1:10 and 1:50 (DNA:lipid, wt:wt), respectively.

Optimal ES cell number for each lipid was determined. Optimal incubation times and conditions were determined (how long and in what buffer gave maximal transfection with both DNA:lipid complexes). Pilot studies indicated that 3–5×10$^6$ ES cells incubated with a 1:50 mixture of DNA-:DOGS in serum free DMEM for 3–4 hours at 37° C. yielded the maximal number of transfectants. These conditions were routinely used for the YAC lipofection experiments.

Neo$^r$ was provided by an unlinked plasmid carrying a PGKneo cassette, either eem or pYPNN, in a co-lipofection procedure. DNA:plasmid molar ratios varied from 1:4 to 1:20. An equal weight of carrier DNA (sheared herring sperm) was also added.

Yeast blocks were prepared at 3.5×10$^9$ cells/ml in 0.67% low gel temp agarose. The YAC was isolated by PFGE. Outer lanes were stained with EtBr and aligned with the unstained portion. A thin slice containing the YAC was isolated using a brain knife. Approximately 1 $\mu$g of YAC was recovered in approximately 10 mls of gel. The gel was washed extensively in gelase buffer (40 mM bis-Tris pH 6.0, 1 mM EDTA, 40 mM NaCl), melted at 70° C., cooled to 40° C., and incubated with 10 U gelase (Epicentre Technologies, Madison, Wis.) overnight.

After digestion, pYPNN or picenter were added at a typical molar ratio of 1:4 (YAC:plasmid). An equal weight of sheared herring sperm DNA was added as carrier. The agarase digestion mix containing approximately 100 mg of the YAC was directly incubated with Transfectam at optimal DNA:lipid ratios for 30 minutes at room temperatures. No polyamines were added.

ES cells were washed, trypsinized, and resuspended in serum free DMEM. Nine mls of cell suspension containing 3×10$^6$ ES cells (and about 10$^5$ feeder cells) were plated onto a 60 mm petri plate (not tissue culture plastic). About 1 ml of the DNA-lipid mix was added to the cells in DMEM and incubated at 37° C. for 3–4 hours. The cells were then collected in DMEM+FBS, and plated at 10$^6$ per 100 mm tissue culture dish. G418 selection was applied 24 hours later, and colonies picked after about 10 days.

Typically, 1–2 $\mu$g of YAC was used per experiment. Thus, about 10–20 separate lipofections were performed on a given day. Generally, several hundred G418 resistant clones were picked, of which at least 1–2% contained specific YAC derived sequence of these, approximately 10% carry the intact YAC, as determined by fine structure southern blotting using probes covering the entire YAC insert, PFGE southern analysis, and PCR analysis.

EXAMPLE 2

Production of mice carrying a YAC encoding human Amyloid Precursor Protein

Preparation of the APP YAC DNA: A 650 kb human genomic fragment containing the full length APP gene was isolated as a yeast artificial chromosome (YAC) in a yeast host strain (clone #B142F9) from the Washington University YAC library (available from Center for Genetics in Medicine Librarian, Washington University School of Medicine, St. Louis, Mo.). The yeast strain was grown to late log phase in AHC medium, resuspended in 0.67% low gelling temperature agarose (SeaPlaque, FMC Corp.) at 3.5×10$^9$ cells/ ml, and cooled in block formers (Bio-Rad). Intact yeast chromosomal DNA was prepared as follows. Thirty 250 $\mu$l blocks of B142F9 cells were swirled in a 150 mm petri dish containing 50 mls of YSS (YSS: 4 mg/ml Novozyme 234 (Novo Nordisk), 1M sorbitol, 100 mM EDTA, 50 mM Potassium Phosphate, pH 5.5) at 37° C. for 30 minutes. The blocks were washed once in TE (10 mM Tris pH 7.5, 1 mM EDTA) and swirled in 50 mls of LDS (LDS: 1% lithium dodecyl sulfate, 1% sarcosyl, 100 mM EDTA) for 30 to 60 minutes at 37° C. The LDS was removed with a sterile 50 ml pipette, and the blocks swirled in 50 mls of fresh LDS overnight. The blocks were rinsed several times in 50 mM EDTA, and stored at 4° C. in 50 mM EDTA. 100 µl segments of the prepared blocks were loaded into each well of a 1% low gelling temp agarose gel in 0.25× TBE (14×25cm CHEF gel, 10 well gel comb, Bio-Rad). The yeast chromosomes were separated by pulsed field gel electrophoresis (CHEF-DRIL, Bio-Rad) using a 60 second switch time at 200V and 14° C. for 48 hours. The end lanes of the gel were removed, stained for 2 hours in 0.5 µg/ml ethidium bromide, and the separated chromosomes visualized on a UV transluminator. Under these conditions, the 650 kb YAC was separated from the nearest endogenous yeast chromosome by 3–5 mm. The gel segments were notched to indicate the location of 650 kb YAC, and the segments realigned with the remainder of the gel. A 2 mm wide slice of the gel containing the 650 kb YAC was isolated using a brain knife (Roboz Surgical Instrument Co) and stored in 50 mM EDTA at 4° C. Approximately 5 µg of YAC DNA was isolated in approximately 10 mls of gel. The agarose slice containing the YAC DNA was equilibrated in gelase buffer (40 mM bis-Tris pH 6.0, 1 mM EDTA, 40 mM NaCl), melted at 70° C. for 20 minutes until completely liquid, and cooled to 45° C. Gelase (25 U, Epicentre Technologies, Madison, Wis.) was added and the molten agarose mixture was incubated at 45° C. for 90 minutes to liquify the DNA-agarose mixture.

Introduction of the APP YAC into ES cells

Embryonic stem cells (AB-1) were washed in PBS, trypsinized, and resuspended in serum free ES medium (DMEM, 1× glutamine, pen/strep, 1 mM 2-mercaptoethanol, 1× NEAA). Approximately $5\times10^6$ cells in 9 ml of serum-free ES cell suspension were placed into each of ten 60 mm petri (non-tissue culture treated) dishes. A linearized plasmid containing a selectable marker (PGKneoA+R, containing the PGK promoter fused to the neomycin resistance gene; Rudnicki et al. (1988) Mol. Cell. Biol. 8: 406; Rudnicki et al. (1989) Biochem. Cell. Biol. 67: 590, incorporated herein by reference) was added to 1 ml of gelase treated YAC DNA at a 2:1 (plasmid:YAC) molar ratio. A cationic lipid (Transfectam, ProMega, Madison, Wis.) was added at a 50:1 (Transfectam:DNA) weight-:weight ratio, the mixture was gently inverted once to mix and incubated at room temperature for approximately 30 minutes. One ml of the DNA:lipid mixture was then added to each 60 mm dish of ES cells and incubated for 4 hours in a 37° C. $CO_2$ incubator. The cells were then transferred to a sterile 250 ml bottle, an equal volume of ES medium (as above, but including 15% fetal calf serum) was added. Cells were removed from the dishes with gentle pipetting and combined with an equal volume of ES medium containing 15 percent fetal calf serum. This cell suspension was transferred in 15 ml aliquots to 100 mm tissue culture plates containing mitotically inactivated SNL76/7 fibroblast feeder cells (McMahon and Bradley (1990) Cell 62: 1073, incorporated herein by reference) and returned to the tissue culture incubator for 24 hours. After 24 hours, the medium was changed to ES medium containing 10 percent fetal calf serum and 400 g/ml G418, and refed every 48 hours. After 7 days, a total of 366 G418 resistant colonies were counted. Each of 240 colonies were individually transferred to a well of a 96-well microtitre dish containing 50 Al of 0.25 percent trypsin in calcium-free magnesium-free PBS. After 15 minutes, 50 µl of serum-containing medium was added, the colony dissociated by trituration, and the cell suspension was transferred to duplicate 96-well plates containing culture medium and feeder layers (as supra). After 4–5 days, one set of dishes was frozen according to conventional methods (Ramirez-Solis et al. Guide to Techniques in Mouse Development (1992) Methods in Enzymology, incorporated herein by reference). Cells were dissociated in 50 µl trypsin and mixed with 50 µof Freezing Medium (20% DMSO, 20% fetal calf serum in DMEM); 100 µl of sterile silicon oil was layered on top of the cell suspension in each well, and the plates were placed in Styrofoam containers and frozen at −80° C.

Identification of ES clones containing APP sequences

The other set of microtitre dishes containing lipofectant ES clones was used to prepare DNA for PCR analysis. 50 µl of lysis buffer (50 mM Tris pH 8.0, 200 mM NaCl, 25 mM EDTA, 0.2% SDS, 1 mg/ml Proteinase K) was added to each well (Ramirez-Solis et al. (1992) Anal. Biochem. 201: 331, incorporated herein by reference). After an overnight incubation at 55° C., 5 µl of 2.5M NaCl and 95 µl of 100% EtOH were added to each well. The dishes were gently swirled at room temperature for 60 minutes to precipitate the DNA. The wells were then rinsed 5 times with 70% EtOH, and dried at 37° C. The DNAs were resuspended overnight in 100l of H2O at 37° C. in a humidified incubator.

Figure 2:
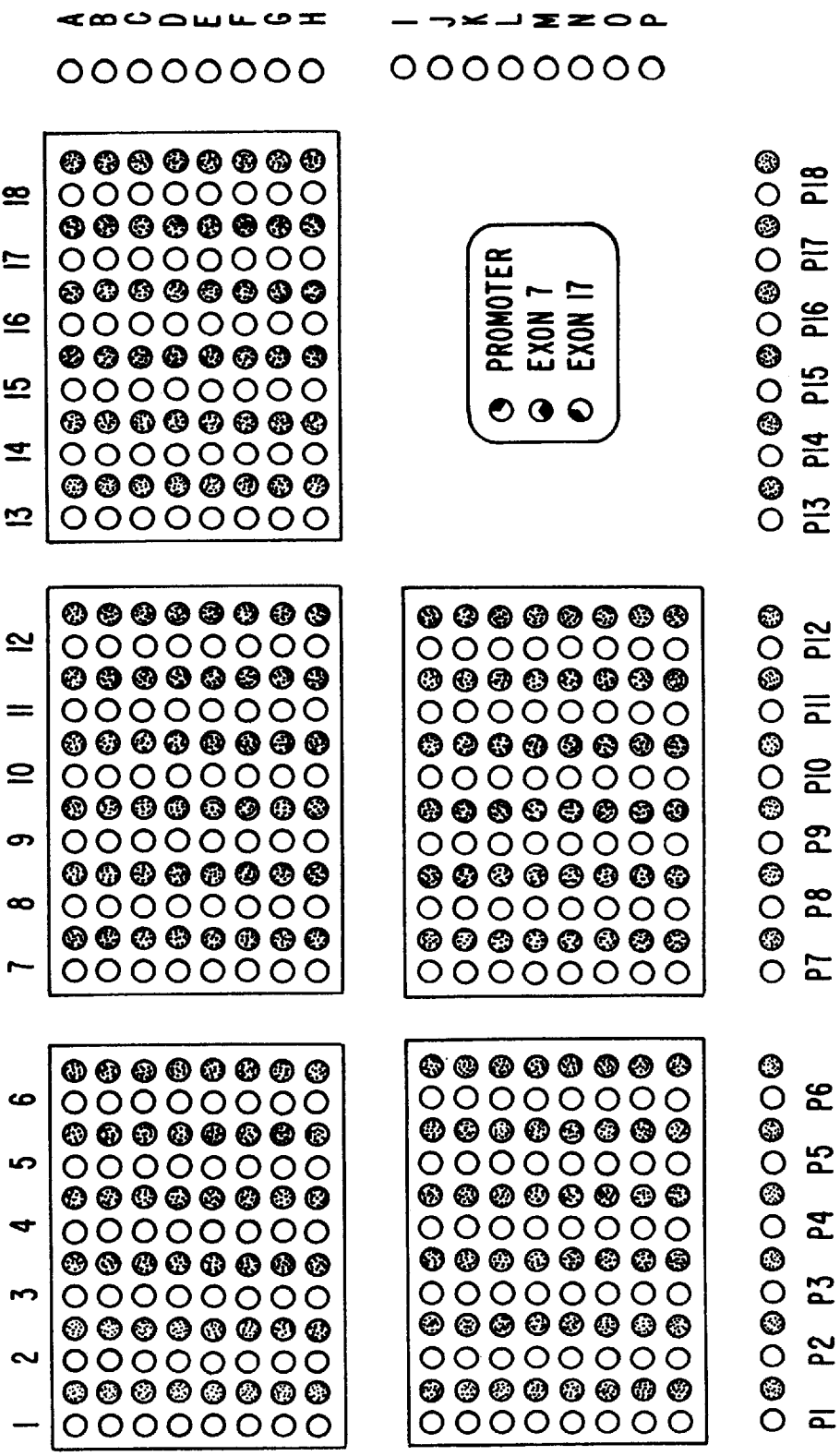
FIG. 2: PCR analysis of ES clones co-lipofected with the human APP transgene. Shaded circles denote wells which were not used. Row pools (A–P) contained 18 (A–H) or 16 (I–P) clones each. Column pools (P1–P18) contained 16 (P1–P12) or 8 (P13–P18) clones each.

The individual DNA samples were pooled in rows and columns for PCR (FIG. 2), and the pools analyzed for APP sequences by PCR, using the following primers (adapted from Fidani et al., Human Molecular Genetics 1, 165–168, 1992):

APP-PA: 5'-GCT TTT GAC GTT GGG GGT TA-3'[SEQ.ID NO:1]
APP-PB2: 5'-TTC GTG AAC AGT GGG AGG GA-3' [SEQ.ID NO:2]
APP-17A: 5'-ATA ACC TCA TCC AAA TGT CCC C-3' [SEQ.ID NO:3]
APP-17B: 5-GTA ACC CAA GCA TCA TGG AAG C-3' [SEQ.ID NO:4]

APP-PA/PB2 denote primers specific for the promoter region of the human APP gene, APP7A/7B are specific for exon 7, and APP17A/17B are specific for exon 17.

Figure 3:
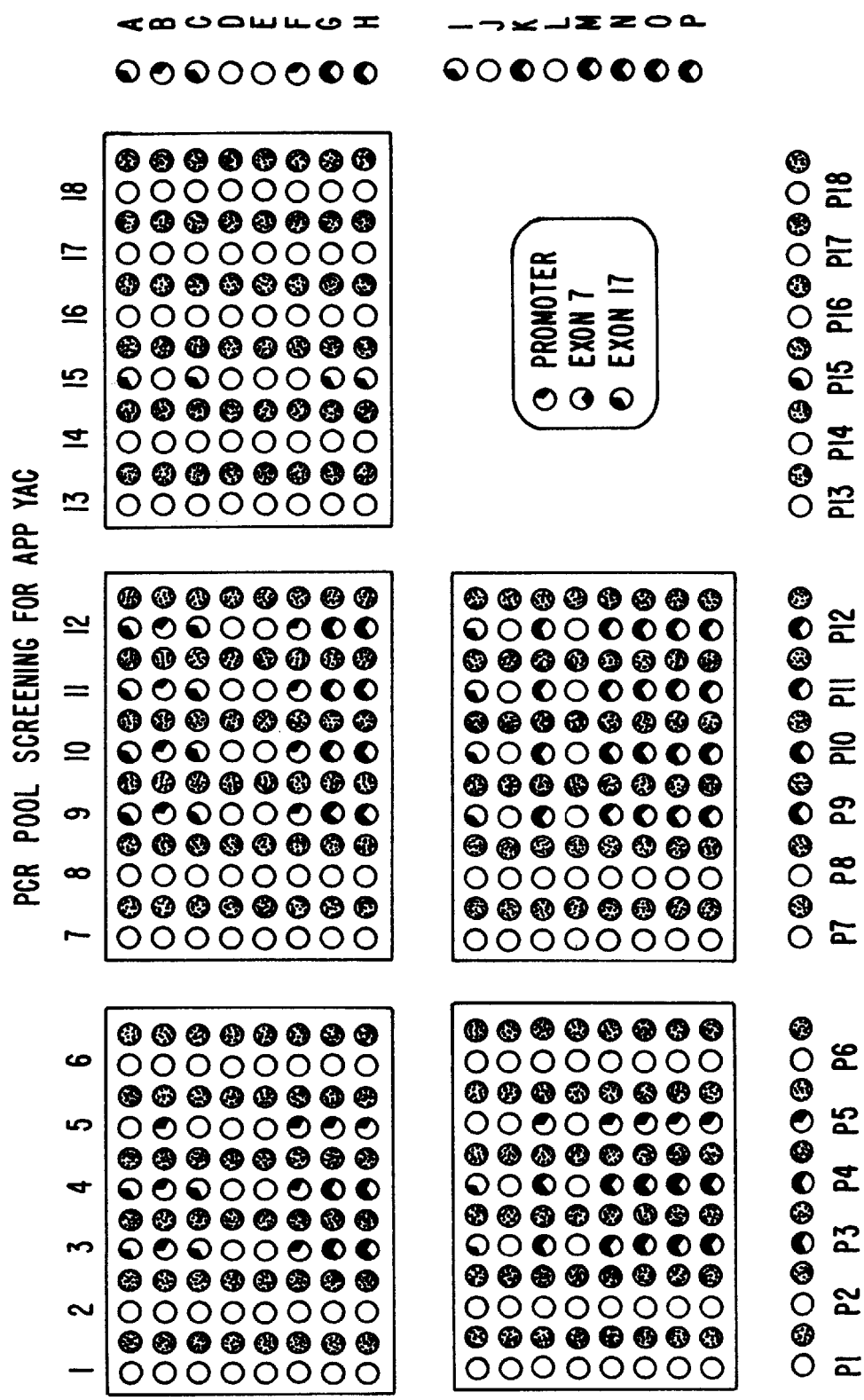
FIG. 3: PCR analysis of ES clones co-lipofected with the human APP transgene. Pools P3, P4, P9, P10, P11, and P12 and pools G, H, K, M, N, O, and P were candidates for containing clones with both promoter and exon 17 sequences.

PCR analysis of the pools indicated 42 clones which potentially carried both promoter and exon 17 sequences (FIG. 3). PCR analysis of the 42 clones individually indicated 6 clones (#s 23, 24, 176, 213, 219, 230) containing both promoter and exon 17 sequences (FIG. 4). These clones were expanded in culture, and frozen in vials in liquid nitrogen. These cells were mounted in agarose blocks for PFGE analysis, and harvested for RNA isolation.

Structural Analysis of ES clones containing APP sequences

The integrity of the APP YAC carried by ES clones was first estimated using a rare cutter fingerprint technique as follows. Restriction enzymes which infrequently cut human DNA were used to define patterns of fragments which hybridized to a human alu fragment probe. Rare cutters often contain the dinucleotide CpG, and mammalian cells often methylate CpG dinucleotides rendering most restriction sites containing them refractory to digestion. However, yeast cells do not methylate CpGs, and thus the pattern of CpG containing restriction sites in a given fragment will depend on whether the fragment is propagated as a YAC in yeast or within a mammalian cell line. Thus, only rare cutter enzymes without CpG in their recognition sequence were used to generate a diagnostic pattern of alu-containing fragments from the YAC.

Figure 5:
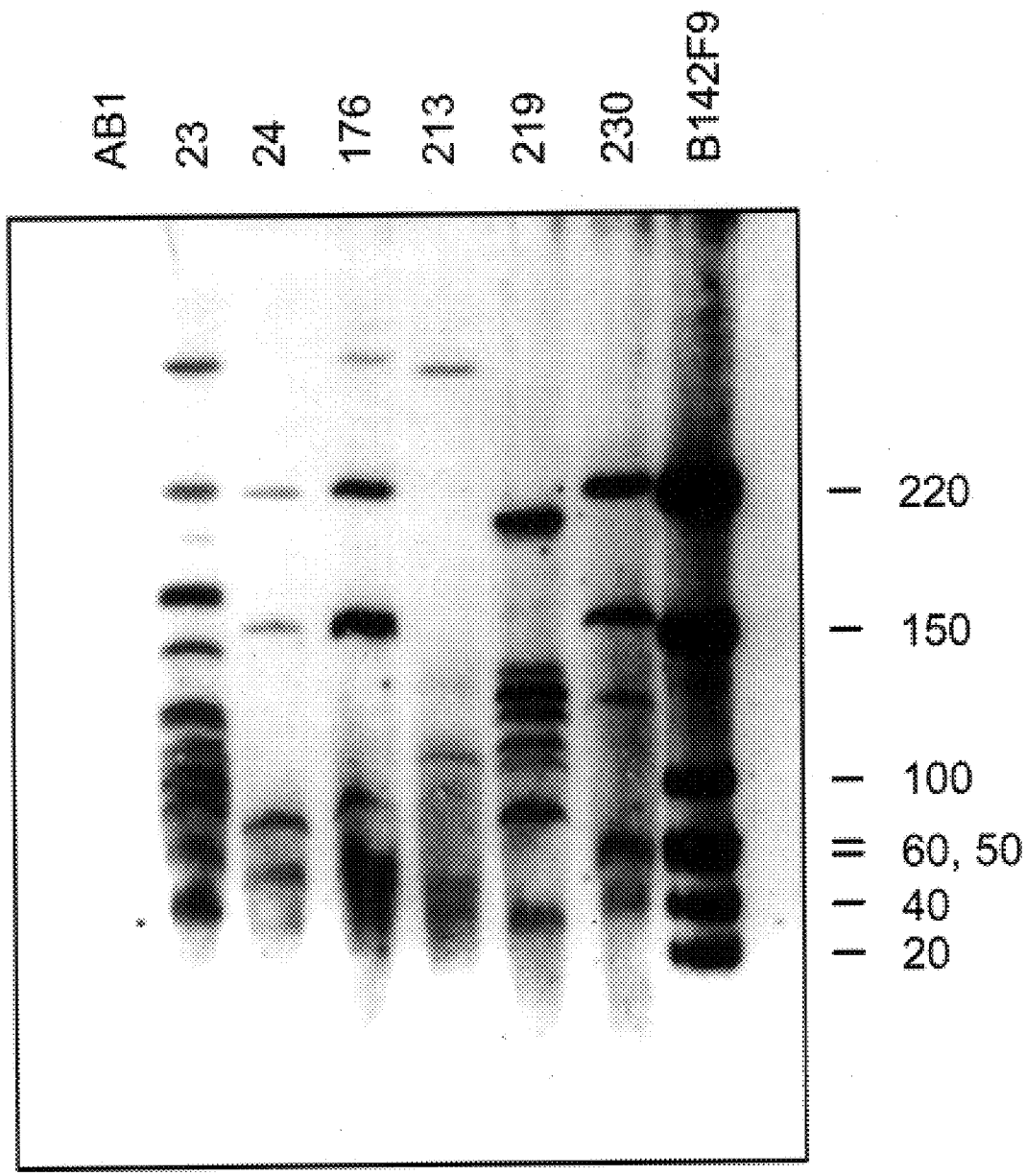
FIG. 5: Southern blot analysis of YAC clone DNA using a human Alu sequence probe.
Figure 6:
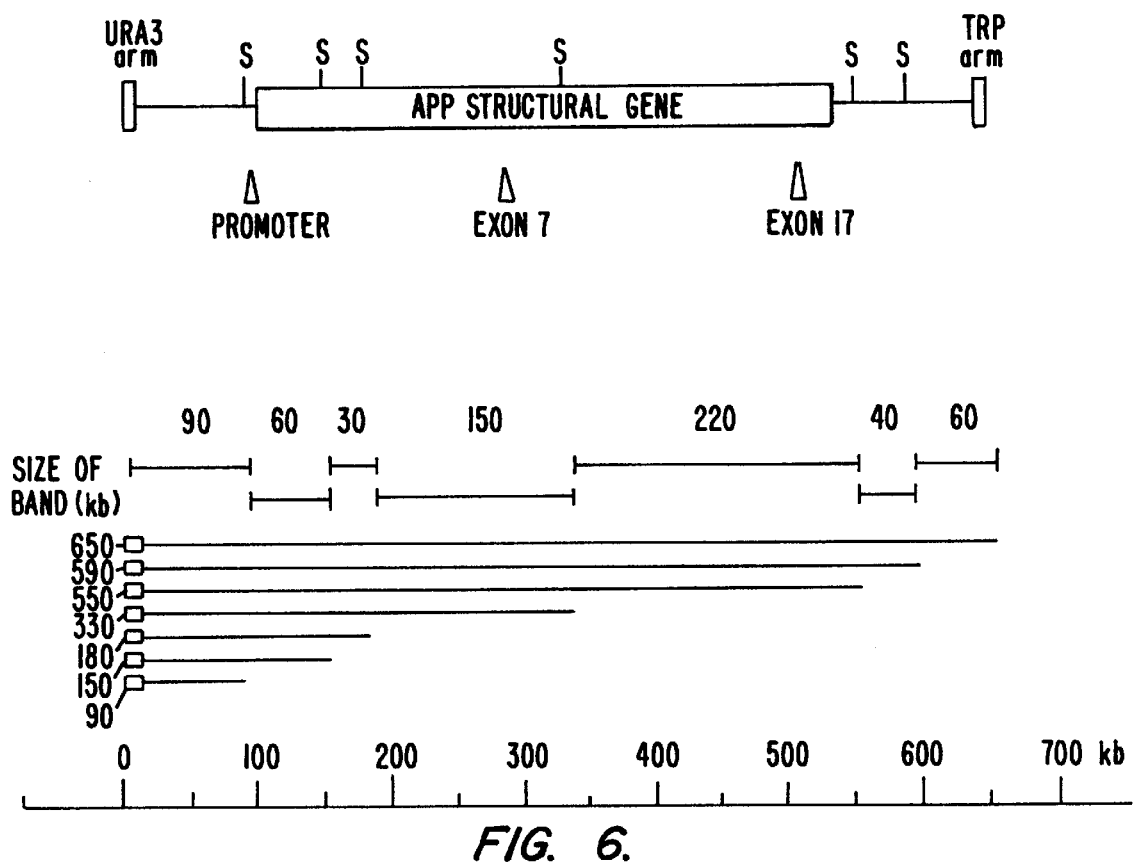
FIG. 6: Partial restriction digest mapping of human APP YAC.

B142F9 agarose blocks were digested completely with the restriction enzymes Sfi I, Pac I, Swa I, Pme I, and Apa I, and analyzed by PFGE Southern blotting using total human DNA as a probe for Alu fragments (FIG. 5). The pattern of bands generated by Sfi I digestion was used as a reference pattern, since there was an even distribution of bands from 30 kb to 220 kb. If a YAC were to integrate intact into ES cells, Sfi I digestion would be expected to generate a similar pattern of bands, with the exception of the terminal fragments. The terminal fragments could be easily identified by reprobing the Sfi I digest with pBR322 sequences. In this case, the entire set of fragments were ordered by partial digest mapping. Briefly, B142F9 blocks were digested with a range of Sfi I concentrations, separated by PFGE, and probed with either the 2.5 kb (trp arm specific) or the 1.6 kb (ura arm specific) Bam HI-Pvu II fragment of pBR322, such that at a particular level of partial digestion, a ladder of bands were generated. Each band differed from its nearest neighbor by the distance to the neighboring Sfi I sites (FIG. 6).

The six ES lines were digested to completion with Sfi I and probed under high stringency conditions with total human DNA of the six lines, only three (24, 176, 230) showed a pattern of bands consistent with the reference pattern from the APP YAC. The rare cutter fingerprinting approach does not require any knowledge of the sequence of the fragment cloned in the YAC, and is thus applicable to the analysis of any YAC containing human DNA. Further, if probes for repetitive elements from other species which were not found in the target mammalian cell line were available, this approach could be used to analyze the structure of YACs containing other foreign DNAs into other mammalian cell lines.

Transcriptional analysis of APP YAC containing ES clones

The six ES lines were analyzed for transcription by PCR. Total RNA was prepared from each cell line by standard guanidium isothiocyanate/lithium chloride procedures (Sambrook et al., Molecular Cloning). Complementary DNA was prepared using an oligo-dT primer, and the cDNAs were analyzed by PCR for splice products of the human APP gene using the PCR primers derived from exons 6 and 9 as depicted below (adapted from Golde et al., Neuron 4 253–267, 1990). To exclude inappropriate amplification of mouse APP cDNAs, the 3' end nucleotide of each oligo was chosen such that it was specific for the human cDNA sequence and not the corresponding mouse cDNA sequence. PCR oligos specific for mouse APP cDNA were also prepared. human APP specific oligos:

APP-HAS1: 5'-CAG GAA TTC CAC CAC AGA GTC TGT GGA A-3'[SEQ.ID NO:5]
APP-HAS2: 5'-CAG GAT CCG TGT CTC GAG ATA CTT GTC A-3'[SEQ.ID NO:6] mouse APP specific oligos:
APP-MAS1: 5'-CAG GAA TTC CAC CAC TGA GTC CGT GGA G-3'[SEQ.ID:7]
APP-MAS2: 5'-CAG GAT CCG TGT CTC CAG GTA CTT GTC G-3'[SEQ.ID:8]

Figure 7:
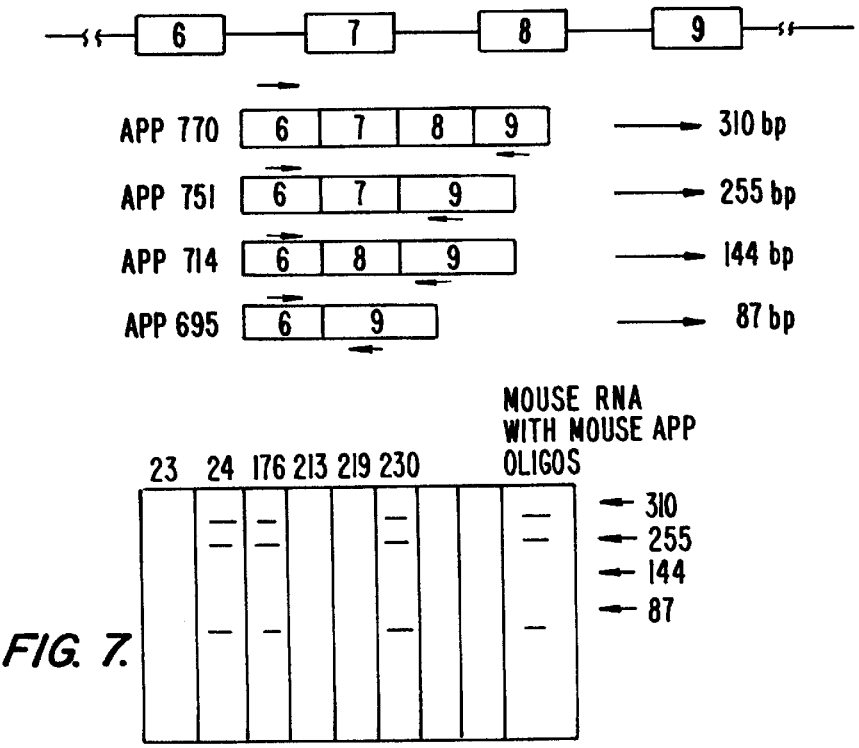
FIG. 7: PCR analysis of RNA transcripts expressed from integrated human APP transgene.

Clones 24, 176, and 230 showed the expected PCR bands indicative of alternatively spliced human APP transcripts encoding the 770, 751, and 695 amino acid forms of the protein (FIG. 7). Clones 23, 213, and 219 did not contain PCR detectable transcript, and also served as a negative control, indicating that the human APP specific oligos did not amplify bands from mouse APP transcripts endogenous to the ES cell lines. Further, the RT-PCR analysis confirmed and validated the results of the rare cutter fingerprint analysis which predicted that clones 24, 176, and 230 contained the intact YAC whereas clones 23, 213, and 219 did not.

Quantitative analysis of APP transcript in ES cells

Figure 8:
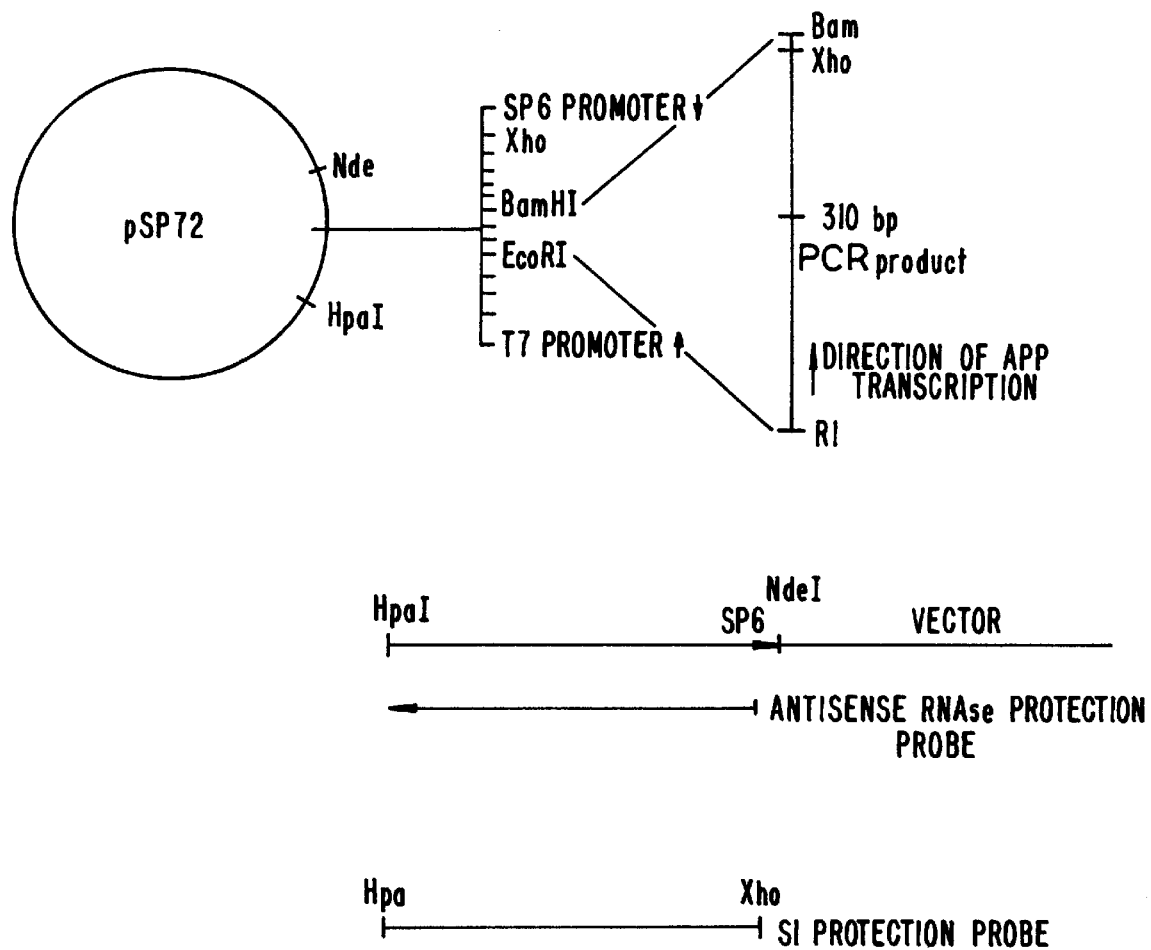
FIG. 8: Quantitative RNase protection assay for detecting APP RNA transcripts from human APP transgene.

Since RT-PCR analysis is qualitative, RNase protection assays are used to quantitate the alternatively spliced human APP transcripts in the ES lines. The RNase probe was generated by cloning the 310 bp RT-PCR product as an Eco RI-Bam HI fragment into the vector pSP72 (FIG. 8). The resultant plasmid, PHAPP, is linearized at the Hpa I site, and antisense transcript is generated from the SP6 promoter. RNase protection assays are performed according to standard protocols (Sambrook et al., Molecular Cloning).

Alternatively, S1 nuclease protection analysis is used to quantitate the transcripts. PHAPP is digested with Xho I and Hpa I to release a 446 bp fragment. The double stranded fragment is end-labelled with Klenow, denatured, hybridized to RNA samples from the ES lines carrying human APP sequences, and S1 analysis performed according to standard methods (Sambrook, et al., Molecular Cloning).

In addition, expression of human APP protein can be determined by immunoprecipitation of human APP using antibodies specific for human APP protein from ES cell lines and tissue of transgenic animals. Such antibodies may also permit direct detection of human APP by standard immunohistochemical analysis of tissue sections.

Analysis of human APP expression in transgenic mice

The qualitative and quantitative assays described above are also applicable to the analysis of the human APP gene in tissues of the transgenic mice derived from these ES lines.

Production of chimeric founders and germline transmission of the APP YAC

Clones 23, 213 and 219 were injected into blastocysts to generate chimeric founder animals as described (Robertson, ed. Teratocarcinomas and Embryonic Stem Cells). Founders are bred to wild type mice to generate F1 animals carrying the APP YAC.

Mouse models of Alzheimer's Disease

Overexpression of the wild type human (or mouse) APP protein may result in phenotypes characteristic of Alzheimer's Disease, including neurofibrillary tangle formation, plaque formation, and neurological dysfunction. Toward that end, different mouse lines expressing the APP YAC can be interbred to increase the number, and hence expression, of human APP genes.

Alternatively, mutations identified as associated with Familial Alzheimer's Disease (codon 717:V->I, F, or G) and/or Hereditary Cerebral Hemorrhage with Amyloidosis, Dutch type (HCHWA-D, codon 693:glu->gln) may be introduced into the human APP gene contained on the YAC using standard yeast molecular genetic techniques such as insertion/eviction of a plasmid carrying a subcloned fragment of the APP gene containing the mutation, or by oligonucleotide directed transformation of yeast (Guthrie and Fink, Guide to Yeast Molecular Genetics and Molecular Biology). YACs carrying these mutated APP genes can be introduced into transgenic mice using procedures described above. Other naturally-occurring human APP disease allele sequences also may be used, including but not limited to those described at codon 692 (Ala ->Gly), codon 692 (Glu ->Gln or Gly), and codon 713 (Ala ->Val) and others that are described (Hendricks et al. (1992) Nature Genet. 1: 218; Jones et al. (1992) Nature Genet. 1: 306; Hardy et al. (1992) Nature Genet. 1: 233; Mullan et al. (1992) Nature Genet. 1: 505; Levy et al. (1990) Science 248: 1124, incorporated herein by reference).

EXAMPLE 3

Transgenic Mice Expressing a Human Immunoglobulin Gene Cloned in a Yeast Artificial Chromosome An 85 kb fragment of the human heavy chain immunoglobulin gene was cloned as a YAC, and embryonic stem cell lines carrying substantially intact, integrated YACs were derived by co-lipofection of the YAC and an unlinked selectable marker. Chimeric founder animals were produced by blastocyst injection and offspring transgenic for the YAC clone were obtained. Analysis of serum from these offspring for the presence of human heavy chain demonstrated expression of the YAC borne immunoglobulin gene fragment. Unlike fusion of yeast spheroplasts with mammalian cells, no yeast chromosomal DNA need be introduced by the co-lipofection method as the YAC(s) are typically first isolated from yeast chromosomes by a separation method, such as pulsed-field gel electrophoresis (PFGE). The YAC was introduced into ES cells by co-lipofection with an unlinked selectable marker plasmid. The co-lipofection strategy differs from lipofection of modified YACs in that retrofitting vectors do not need to be constructed or recombined into the YAC, and YACs carried in recombination deficient hosts can be used. In contrast to microinjection approaches, it is likely that larger YACs can be introduced by co-lipofection than microinjection due to the technical hurdles in purification of intact YAC DNA and because of the high shear forces imparted on the DNA during microinjection. Furthermore, unlike fusion of yeast spheroplasts with mammalian cells where some of the yeast chromosomes integrate with the YAC[5, 6], no yeast chromosomal DNA is introduced in co-lipofection since the YAC is first isolated by pulsed field gel electrophoresis.

Transgenic mice were produced by blastocyst injection of ES cells carrying an intact YAC. The YAC was maintained intact through the germline, and human heavy chain antibody subunits were detected in the serum of transgenic offspring.

Human Heavy Chain Gene Fragment

The 85 kb Spe I fragment of the unrearranged human immunoglobulin heavy chain locus was isolated. The 85 kb Spe I fragment of the human heavy chain immunoglobulin (H) chain gene contains at least one of each element required for correct rearrangement and expression of a human IgM heavy chain molecule.

Cloning of J1.3P

An 85 kb Spe I restriction fragment of the human heavy chain immunoglobulin gene contains $V_H^6$, the functional diversity (D) segments, all six joining (J) segments, and the $C\mu$ constant region segment (Hofker et al. (1989) *Proc. Natl. Acad. Sci.* (*U.S.A.*) 86: 5587; Berman et al. (1988) *EMBO J.* 7: 727; Shin et al. (1991) *EMBO J.* 10: 3641). Fresh human sperm was harvested and genomic DNA prepared in agarose blocks as described in Strauss et al. (1992) *Mamm. Genome* 2: 150). A size selected (50–100 kb) Spe I complete digest YAC library was prepared in the yeast host strain AB1380 in pYACneo[15], using the Spe I site near the centromere as the cloning site. A size selected (50–100 kb) Spe I complete digest YAC library was produced in the YAC vector pYACneo[15] and screened by colony hybridization with a probe specific for human $\mu$ (Traver et al. (1989) *Proc. Natl. Acad. Sci.* (*U.S.A.*) 86: 5898). One positive clone (J1) was identified among approximately 18,000 primary transformants. Because yeast mitochondrial DNA often obscured the YAC on pulsed field gel electrophoresis, a r° petite variant lacking mitochondrial DNA was selected by EtBr treatment, and denoted J1.3P. One subclone, J1.3P, was mounted in agarose blocks at $3.5 \times 10^9$ cells/ml and intact yeast chromosomal DNA was prepared (Smith et al. (1990) *Proc. Natl. Acad. Sci.* (*U.S.A.*) 87: 8242). The YAC DNA was isolated in a 3–4 mm wide gel slice from a low melting point preparative CHEF gel (Biorad). The gel slice was equilibrated in b-agarase buffer (Gelase, Epicentre Technologies), melted at 70° C. for 20 minutes, cooled to 45° C., and digested with 10 units of agarase overnight at 45° C.

Characterization of YAC J1.3P

The authenticity of the J1.3P insert was determined by restriction mapping and Southern analysis. The ends of the insert were subcloned, using the bacterial selectable markers in the centromeric and acentromeric arms of pYACneo. Fine structure restriction analyses of the terminal fragments were entirely consistent with published maps and sequences of the region (Fox et al. *Analysis and manipulation of yeast mitochondrial genes,* In *Guide to Yeast Genetics and Molecular Biology* (1991) eds. Guthrie C and Fink G, Academic Press, San Diego, Calif.; Word et al. (1989) *Int. Immunol.* 1: 296) and defined the orientation of the insert with respect to the vector arms. The orientation was further verified by PCR analysis of the acentromeric insert for $V_H 6$ sequences, and hybridization of the centromeric insert with the $C\mu$ probe. Southern analysis of the $C\mu$ region was consistent with published maps and restriction analyses (Hofker et al. (1989) *Proc. Natl. Acad. Sci.* (*U.S.A.*) 86: 5587). The functional diversity segments of the human heavy chain are contained in a 35 kb span containing a four-fold polymorphic repeat of D segments. Southern analysis of the J1.3P YAC produced a "restriction fragment fingerprint" of the D region in which all of the D specific bands in the YAC were present in human genomic DNA.

Co-lipofection of J1.3P YAC into ES cells

The J1.3P YAC was co-lipofected with an unlinked linearized plasmid carrying the neor gene driven by the mouse PGK promoter (Soriano et al. (1991) Cell 64: 893).

Selectable marker plasmids

Plasmid is a 5 kb plasmid containing an expression cassette consisting of the neo gene under the transcriptional control of the mouse phosphoglycerate kinase-1 promoter and the PGK-1 poly (A) site (Tybulewicz et al. (1991) *Cell* 40: 271). The plasmid pYPNN is a variant of pYACneo containing the PGKneo cassette in place of the SV40 promoter-neor cassette, constructed by exchange of a 4.5 kb Sal I-Apa I fragment of pYACneo for a 1.5 kb Sal I-Apa I fragment of a containing the PGK promotor, neor coding region, and the PGKp(A) signal. The plasmids were linearized with Sal I (a) or Not I (pYPNN).

Lipofection of YAC DNA into ES cells.

The digested agarose/DNA mixture was divided into 1 ml (approximately 100 ng) portions in polystyrene tubes (Falcon) and 100 ng pYPNN or 20 ng , and 1 $\mu$g sheared herring sperm DNA (Sigma) was mixed in each tube, and cationic lipid (Transfectam, ProMega) was then added at a 10:1 ratio (wt:wt) and gently mixed into the DNA solution. The mixture was incubated for 30 min at room temperature to allow formation of DNA-lipid complexes. Rapidly growing confluent cultures of AB-1 embryonic stem (ES) cells on mitotically inactivated SNL 76/7 fibroblast feeder layers were trypsinized to yield a single cell suspension, washed with serum-containing medium, and resuspended in serum-free DMEM (Gibco).

For each lipofection, 9 ml of cell suspension containing $3 \times 10^6$ ES cells and about $1 \times 10^5$ feeder cells were mixed with 1 ml of the DNA-lipid mixture in a 60 mm petri dish (Falcon 1007; Becton Dickinson) and incubated for 4 hours at 37° C. in a humidified 5% CO2 atmosphere. Dishes were swirled gently during the incubation to minimize cell attachment. After incubation, cells were diluted with serum-containing ES cell medium, dispersed gently, and plated at $1 \times 10^6$ on 100 mm culture dishes containing feeder layers. Cells were selected in G418 (400 $\mu$g/ml powder, Gibco) for 9–12 days, beginning 24 hours after plating. Two different plasmids were tested: pYPNN (a 12 kb derivative of pYAC-neo carrying the PGKneo cassette in place of the SV40-neo cassette) and ickensian (a 5 kb plasmid carrying the same PGKneo cassette). The YAC:plasmid molar ratio was 1:8 for pYPNN and 1:4 for ickensian. Two cationic lipid formulations were tested, DOGS (Transfectam; ProMega) and DOTMA (Lipofectin; BRL). Similar transfection efficiencies were obtained for DOGS and DOTMA with linearized plasmids, but DOGS was ultimately chosen for the YAC experiments because its cationic moiety is spermine, obviating the need for exogenously added spermine as a DNA protectant, and because DOGS was not toxic to ES cells at the concentrations used. Because the DNA:lipid ratio was found to be important to the transfection efficiency, and precise measurement of the YAC DNA concentration was difficult, each lipofection contained an estimated 10-fold excess (1 $\mu$g) of sheared herring sperm carrier DNA to provide a baseline level of DNA.

Analysis of ES clones

G418-resistant clones were dispersed with trypsin and the cells from each clone were divided into one well of a 96-well plate that was frozen and a second 96-well or 24-well plate used for preparation of DNA for screening by Southern analysis. Positive clones were thawed and expanded for further analysis.

Southern blot hybridization and PCR Genomic DNA was prepared from ES cells and tail biopsies by rapid preparation methods (Laird et al. (1991) *Nucleic Acids Res.* 19: 4293) and subjected to Southern analysis by standard methods. For pulsed field gel electrophoresis, ES cells were embedded in agarose blocks at $10^7$ cells/ml, prepared for restriction digestion, and digested overnight with Spe I. For Southern analysis of pulsed field gels, the DNA was acid-nicked, then transferred to GeneScreen Plus (DuPont) in denaturing solution (0.4N NaOH, 1.5 M NaCl). Oligonucleotides suitable for PCR amplification of the VH6 region were prepared from published sequences. Primers used were 5'CAGGTACAGCTGCAGCAGTCA3[SEQ.ID.NO.7] and 5'TCCGAGTCACAGAGTTCAGC3'[SEQ.ID.NO.10] which amplified a diagnostic 275 bp product.
Production and analysis of transgenic mice Clones containing intact YAC sequences were injected into blastocysts to produce chimeric founder animals, which were bred with C57BL/6 wild type mice and $J_H$- mice, which carry targeted inactivations of both copies of the mouse heavy chain gene. Thymic cells from transgenic offspring were mounted in agarose blocks for pulsed field gel electrophoresis and Southern analysis to confirm transmission of the intact YAC.

ELISA assays

Human mu chain was detected using a 2-site ELISA assay. Polyvinyl chloride microtiter plates were coated with mouse monoclonal anti-human IgM clone CH6 (The Binding Site, San Diego, Calif.) at 1.25 $\mu$g/ml in 100 $\mu$l PBS by overnight incubation at 4° C. Plates were blocked by 1 hr incubation with 5% chicken serum (JRH, Lexana, Kans.) in PBS. Following 6 washes with PBS, 0.5% tween-20, serum samples and standards were diluted in 100 $\mu$l PBS, 0.5% Tween-20, 5% chicken serum (PTCS) and incubated in the wells for 1 hr at room temp. Purified human myeloma-derived IgM, kappa (Calbiochem, La Jolla, Calif.) was used as a standard. Plates were then washed 6 times with PBS, 0.5% tween-20 before addition of peroxidase conjugated rabbit anti-human IgM, Fc5u fragment specific antibody diluted 1/1000 in 100 $\mu$l PTCS. After another 1 hr incubation at room temperature, the wells were washed 6 times and developed for ½ hr with 100 $\mu$l ABTS substrate (Sigma) Assay plates were read at 415–490 nm on a Vmax microplate reader (Molecular Devices, Menlo Park, Calif.), and IgM concentration determined from a 4-parameter logistic curve fit of the standard values. A level of 4.89 ng/ml in serum samples is routinely detected by this assay and differentiated from background by at least 3 standard deviations.

Results

Approximately eight $\mu$g of J1.3PYAC DNA were lipofected in eight separate experiments of the 1221 G418 resistant clones screened, 15 contained the two diagnostic Eco RI C$\mu$ fragments. Two of the clones (#s 195 and 553) contained only one of the two C$\mu$ bands, which may have arisen from fragmentation of the YAC within the missing Eco RI fragment. The two selectable marker plasmids, pYPNN and ace, produced, respectively, frequencies of 0.5 and 13.5 G418 resistant clones per $10^6$ transfected cells; the efficiency of PYPNN selection was much lower even though it was used at twice the molarity of ace. It is unclear why the plasmids differed, since they both contained the same neor cassette, but it may be a consequence of the extent of sequence homology between the plasmid and the vector arms, or different efficiencies of neor expression from the two plasmids.

Analysis of YAC structure in ES cells.

The four C$\mu^+$ clones from the pYPNN co-lipofections (#s 12,14,18,21) were analyzed for D region structure by the restriction fragment fingerprint assay described above. Of the four clones, only clone 18 retained the fingerprint of the parent YAC. Clones 14 and 21 contained fewer bands than the parent, suggesting that YAC sequences may have been lost, while clone 12 contained several additional bands, consistent with integration of more than one copy of the YAC in this ES line.

The integrity of the 3' end of the insert region in the four ES lines was assessed by Southern analysis using the 10.5 kb Nde I-Spe I terminal fragment isolated by vector recircularization as probe. Three bands are expected from a Xho I digest of the parent YAC: a very large D-J-C$\mu$ band (>30 kb), a 4.5 kb C$\mu$-C$\delta$ band, and an 8.9 kb C$\delta$-vector band. A double digest with Xho I and Spe I is expected to reduce the size of the 8.9 kb band to 4.1 kb. The 4.5 kb and 8.9 bands are present in the Xho I digests, while the 4.5 kb and 4.1 kb bands are present in the Xho I-Spe I digests of the parent YAC. Among the four ES lines, only line 18 contained the parental YAC banding pattern indicative of an intact 3'-end. The presence of an 8.9 kb band is consistent with the retention of the vector arm Xho I site in the ES line, suggesting that very little of the telomeric region had been lost in this clone. Loss of YAC terminal sequences would be expected to result in aberrant Xho I bands. Among the other three ES lines, clone 14 lacked the 4.5 kb Xho I band, while clones 12 and 21 contained aberrantly short Xho I bands, indicating rearranged or deleted 3' end regions in these ES clones. A similar analysis of 5' end integrity was not possible due to repetitive elements in the region. However, PCR and Southern analysis using the VH$^6$ PCR product as probe indicated that clone 18 contained VH$^6$ sequences, while clones 14, 12, and 21 did not.

Of the 13 C$\mu^+$ ES cell lines from the d co-lipofections, one was lost during clonal expansion, and one (#266) was eliminated because it lacked VH⁶ sequence. The remainder were analyzed for D region structure, 3'-end integrity and/or $V_H^6$ sequence. Of the 11 lines analyzed for D region fingerprint, six (#s 86, 191, 220, 371, 463, 567) showed an intact D region while five had aberrant patterns. 3' end analysis of five of the six lines with intact D regions revealed that all but one (#220) contained an intact 3' end. PCR analysis revealed that five of the six lines with intact D regions (#86, 220, 371, 463, 567) contained $V_H^6$ sequences, while only one of five lines without intact D regions (#35) contained $V_H^6$ sequences.

Ten of the ES cell lines were examined for full length insert by pulsed field Southern analysis using the D region or Cμ probe. Only clones 18, 371, and 463 contained an 85 kb Spe I fragment indicative of a full length insert; all of the other clones had a smaller Spe I fragment. The Spe I digest of clone 18 was screened with both D and Cμ probes and a probe for $V_H^6$; all three probes hybridized to a single band of 85 kb.

The pulsed field Southern analysis, taken together with the D region, 3' end and $V_H^6$ fine structure analyses, indicate that the YAC insert was transferred intact in three ES lines: #18, #371, and #463. A high degree of internal rearrangement, deletion or fragmentation was generally seen in the ES lines carrying disrupted YAC sequences, although subtle alterations of structure were also detected (e.g., #567). Overall, the frequency of intact YAC transfer was low, 1 in 400 G418$^r$ clones (3/1221). However, the isolation of the clone DNAs and the primary screen for Cμ sequences (which eliminated 1206 of the 1221 clones from further analysis) were rapidly performed using the microtitre plate protocols described in Methodology. Thus, only 15 clones required extensive analysis.

Molecular analysis of YAC structure in ES cells is greatly facilitated by a low, preferably single, copy of the YAC. The D region, pulsed field gel analysis, and 3' end analyses of the ES lines are consistent with a low or single copy integration of the YAC. Analysis of clones 18, 371, and 463 for a diagnostic 3' end flanking band showed that clones 18 and 371 carried a single copy of the YAC insert, while 463 may have an additional intact or partially intact copy.

Production of chimeras and germline transmission of the YAC

Blastocysts were injected with ES lines 18, 371, and 463. Chimeric founder animals ranging from 10% to 95% ES cell contribution to coat color were derived from all three lines. The oldest animal, a 40% chimeric male derived from ES line 18, transmitted the ES cell genotype to 20 of 73 offspring. Eleven of the 20 agouti offspring were positive for an intact D region fingerprint, consistent with Mendelian segregation of a hemizygous YAC transgene allele. In addition, pulsed field Southern analysis using the D region probe demonstrated a single 85 kb Spe I band in transgenic offspring, indicating that the YAC was stably maintained through the germline. Thus, co-lipofection of YACs into ES cells does not abrogate ES cell totipotency.

Southern analysis of integration sites for the co-lipofected selectable marker indicated integration of 2 to 10 plasmid copies. Because it is possible that the marker plasmids could be a source of mutations if they were to insert at multiple loci, the integration sites of the plasmid were tracked by Southern analysis for plasmid sequences. Since pYPNN and the YAC vector arms lack Eco RI sites and contain pBR322 sequences, each Eco RI band which hybridized to a pBR322 probe represents the integration of a separate intact or fragmented copy of PYPNN or the YAC vector arms. Analysis of ES cell clone 18 DNA revealed eight Eco RI bands ranging in size from 5.5 kb to 20 kb, and the offspring of a hemizygous transgenic animal bred with non-transgenic mates were analyzed for segregation of the Eco RI bands. Among 14 offspring, all eight Eco RI bands were detected in tail DNAs of the 9 transgenic pups, and none were detected in tail DNAs of the 5 non-transgenic pups. Thus, all detectable marker plasmids segregated with the YAC, indicating that they had inserted at or near the YAC integration site. Co-integration of different DNAs have been observed in transgenic mice produced by microinjection of zygotes, and it is expected that co-integration of plasmid DNAs would be no more mutagenic for co-lipofection than for zygote microinjection. Presumably, the herring sperm carrier DNA had also co-integrated with the YAC, and may be a source of Eco RI sites in the Southern analysis. Since co-integrated carrier DNA may potentially adversely affect YAC transgene function, it is frequently preferable to omit carrier DNA. Preliminary experiments with a 650 kb YAC indicate that carrier DNA is not required for efficient lipofection of intact YACs into ES cells. This preliminary work also suggests that the size limit of YACs which can be successfully co-lipofected into ES cells is at least 650 kb.

Serum expression of human immunoglobulins in transgenic mice

Line 18 transgenic mice were assayed for human mu chain in the serum by ELISA. Human mu heavy chain was detected in the serum of transgenic offspring (Table 3). Although the human mu serum levels in the transgenics were clearly within the detectable range, they were very low compared to serum levels of endogenous mouse IgM. The low level of transgene expression is due in part to competition from the endogenous heavy chain gene. The transgene was introduced into a background in which the endogenous heavy chain alleles are inactivated, and in this mouse, the human mu serum levels were elevated approximately 10 fold (Table 3).

TABLE 3

Detection of serum human IgM by ELISA

| Genotype | Sex | Age at assay (wk) | Human IgM |
|---|---|---|---|
| YAC 18+ | F | 3, 9, 20 | <5 ng/ml |
| YAC 18+ | M | 17 | 12.2 ng/ml |
| YAC 18+ | F | 10 | 27.0 ng/ml |
| YAC 18+ | F | 6, 17 | <5 ng/ml |
| YAC 18+ | F | 4 | 5.8 ng/ml |
| YAC 18+ | F | 6 | 10.5 ng/ml |
| YAC 18+ | M | 6 | 10.4 ng/ml |
| YAC 18+/J$_H$- | M | 5, 8 | 165 ng/ml |
| Wild type | F | 6 | <5 ng/ml |
| Wild type | F | 6 | <5 ng/ml |
| Wild type | F | 6 | <5 ng/ml |
| Wild type | M | 6 | <5 ng/ml |
| Wild type | F | 34 | <5 ng/ml |
| Wild type | F | 34 | <5 ng/ml |
| Wild type | M | 34 | <5 ng/ml |

TABLE 3-continued

Detection of serum human IgM by ELISA

| Genotype | Sex | Age at assay (wk) | Human IgM |
|---|---|---|---|
| Wild type | M | 34 | <5 ng/ml |

Table 3. Blood samples from transgenic animals and controls were analyzed by ELISA for human IgM at the ages indicated. All of the transgenic animals are derived from a single clone 18 founder chimera, and are hemizygous for the YAC (YAC 18+). Five of the seven animals in a wild type background had detectable human IgM in their serum. The level of detection of the ELISA was 5 ng human IgM/ml serum. The serum human IgM level was elevated approximately 10-fold when the YAC transgene was bred into a background lacking functional endogenous mouse heavy chain genes (YAC18+/$J_H$-).

FACS Analysis of YAC+/JH- Mice

Fluorescence-activated cell-sorting (FACS) analysis was performed on mice positive for the YAC containing the 85 kb heavy chain gene fragment and homozygous for a functionally disrupted ("knocked-out") endogenous murine immunoglobulin heavy chain gene by disruption of the JH region by homologous gene targeting. The mice had a single copy of the YAC transgene and lacked functional murine heavy chain alleles. The FACS analysis used antibodies to detect human mu chains, among others, and showed that about 60 cells per 10,000 total peripheral lymphocytes from the mice expressed a human mu chain immunoglobulin. This level is approximately 1–2 percent of the number of cells that express murine mu chains in a wild-type (non-transgenic/non-knockout) mouse spleen.

FACS detected human mu chain expression in cells obtained from the spleen and peritoneal cavity of the YAC+/$J_H$- mice.

EXAMPLE 4

Figure 9:
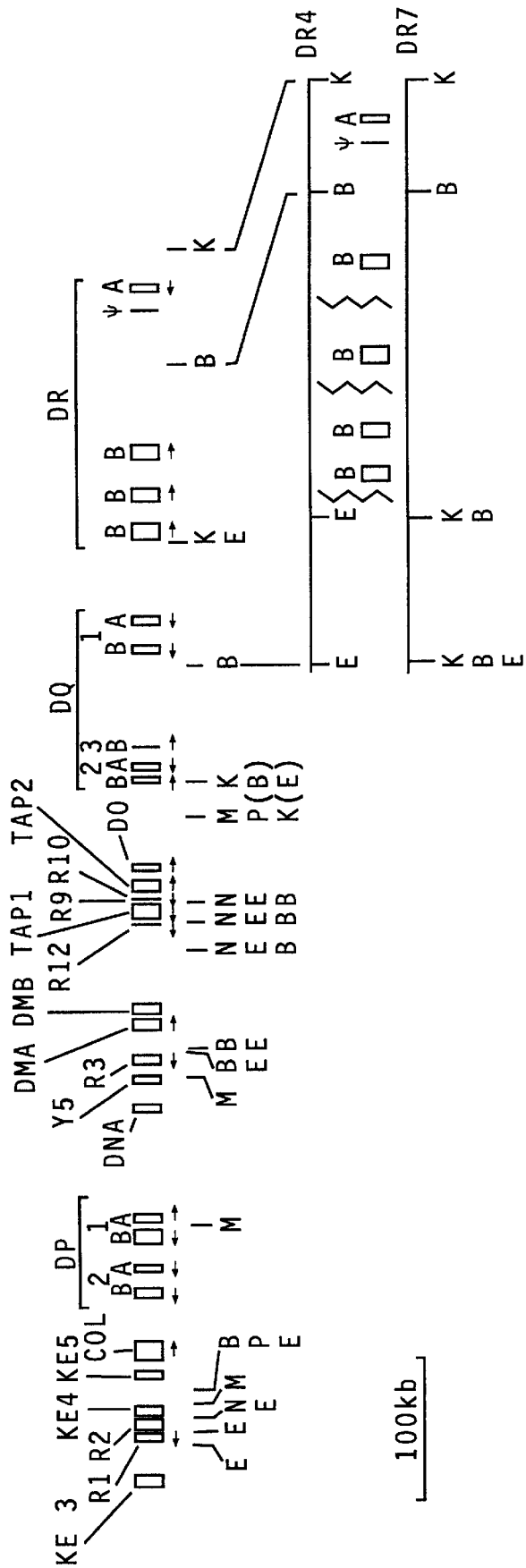
FIG. 9: Map of human MHC Class II region.

Production of mice carrying a YAC encoding the human major histocompatibility (MHC) locus Class II region Preparation of the MHC Class II YAC A 550 kb human genomic fragment spanning a portion of the major histocompatibility locus and including the DRa/b, DQa/b, DOB, TAP1/TAP2, and LMP2/LMP7 (also known as Ring 10/12, respectively) genes, was isolated as a yeast artificial chromosome (YAC) designated clone 4D1, in a yeast host strain AB1380 (Ragoussis et al. (1992) *Nucl. Acids Res.* 20: 3135). FIG. 9 shows a map of the MHC Class II region (from Campbell (1993): "The Human Major Histocompatibility Complex: A 4000-kb Segment of the Human Genome Replete with Genes", in: *Genome Analysis, vol. 5*: Regional Physical Mapping. Cold Spring Harbor Press). DRa/b and DQa/b genes encode highly polymorphic proteins important for the growth and differentiation of T and B lymphocytes, antigen presentation, cytotoxicity, graft rejection, and mixed lymphocyte reactions. The TAP1/2 proteins are involved in the transport of cytosolic antigens to the endoplasmic reticulum where they assemble with a MHC Class I heavy chain plus β2-microglobulin (reviewed by Monaco (1992) *Immunology Today* 13: 173). The LMP2/7 proteins are thought to function within a low molecular mass polypeptide (LMP) complex that cleaves proteins into peptides which bind to MHC Class I molecules.

Isolation of the 4D1 YAC was performed as described in Example 2, with minor changes. The yeast strain was grown to late log phase in AHC medium at 30° C., pelleted and rinsed once in distilled water. After centrifugation, the pellet was resuspended in YSS without novozyme, plus 0.67% low gelling temperature agarose (SeaPlaque, FMC Corp.) at $3.5 \times 10^9$ cells/ml, and cooled in block formers (Bio-Rad). Cooled blocks were transferred into 50 ml YSS (including novozyme at 4 mg/ml) and rotated for one hour at room temperature. The solution was replaced by LDS and blocks swirled for 30–60 minutes at room temperature. Fresh LDS was then added and the blocks swirled overnight at room temperature. The following day, LDS was replaced a final time for one hour, and the blocks then rinsed three times for 30 minutes/each in 50 mM EDTA and then stored at 4° C. in 50 mM EDTA. For isolation of intact YAC DNA, 10 yeast blocks were transferred side by side into a single long well of a 1% low gelling temperature agarose gel in 0.25× TBE (14×25 cm CHEF gel). The yeast chromosomes were separated by pulsed filed gel electrophoresis (CHEF-DRIL, Bio-Rad) using a 50 second switch time at 200V and 14° C. for 40 hours. The end and middle portions of the gel were removed, stained for 2 hours in 0.5 mg/ml ethidium bromide, and visualized on a UV transluminator. Under these conditions, the 550 kb YAC was separated from the nearest YAC chromosomes by 2–4 mm. The gel segments were notched to mark the location of the 550 kb YAC, and the segments realigned with the remainder of the gel. A gel slice approximately 2 mm wide was removed using a brain knife (Roboz Surgical Instrument Co) and stored in 50 mM EDTA at 4° C.

For lipofection into ES cells, the gel slice containing the 550 kb YAC was equilibrated in gelase buffer, melted at 70° C. for 20 minutes until completely liquid, and cooled to 45° C. Gelase was added at 10 units per gram of gel slice and incubated for one hour at 45° C. Gelase was added a second time and incubated for another hour to ensure the molten agarose mixture was liquefied.

Introduction of the MHC Class II YAC into ES cells

Lipofection procedures were similar to those outlined in Example 2, with modifications. A linearized plasmid containing a selectable marker (PGKneoA+R) was added to the YAC DNA at a 4:1 molar ratio. A cationic lipid (Transfectam, ProMega, Madison, Wis.) was added at a 50:1 (Transfectam:DNA) weight:weight ratio, the mixture was gently inverted once to mix, and incubated at room temperature for approximately one hour at room temperature. Embryonic stem cells (AB-1) were washed in PBS, trypsinized, and resuspended in serum free ES medium (DMEM, 1× glutamine, pen/strep, 1 mM 2-mercaptoethanol, 1× NEAA). Approximately $3 \times 10^6$ cells in 9 ml of serum free medium was added to 20 60 mm petri dishes. Each dish received 1 ml of the DNA/lipid mixture and the cells incubated in a $CO_2$ incubator at 37° C. for 4 hours. Cells were transferred into tissue culture plates containing mitotically inactivated SNL76/7 fibroblast feeder cells and cultured under selective media as described in Example 2. After 11 days, a total of 426 G418 resistant colonies were counted. Each of 424 colonies were individually transferred to a well of a 96-well microtitre dish, trypsinized, and split equally into 3 sets of 96-well microtitre plates containing feeder cells (as supra). After 4–5 days, two sets of plates were frozen at −80° C.

Identification of ES clones containing MHC Class II sequences

The other set of microtitre plates was used to prepare DNA for PCR analysis. DNA from individual wells was resuspended in 30 ul distilled water. Five microliters was added separately to reaction tubes for PCR amplification as described for the Boehringer Mannheim PCR kit (1578553): 80.5 ul DW, 10 ul 10× buffer, 2 ul dNTP mixture, 0.5 ul Taq DNA polymerase, 1 ul of 7.5uM primers, 5 ul DNA. The following primers were used for the TAP1(Colonna et al. (1992) *Proc. Natl. Acad. Sci.* 89: 3932), DQb, and DRb (Erlich and Bugawan (1989) "HLA Class II Gene Polymorphism: DNA Typing, Evolution, and Relationship to Disease Susceptibility," in: Erlich, ed., *PCR Technology.* Stockton Press) genes:

```
TAP1  A: 5' - CAC CCT GAG TGA TTC TCT - 3'
      B: 5' - ACT GAG TCT GCC AAG TCT - 3'
DQb   A: 5' - CTC GGA TCC GCA TGT GCT ACT TCA CCA ACG - 3'
      B: 5' - GAG CTG CAG GTA GTT GTG TCT GCA CAC - 3'
DRb   A: 5' - CCG GAT CCT TCG TGT CCC CAC AGC ACG - 3'
      B: 5' - CTC CCC AAC CCC GTA GTT GTG TCT GCA - 3'
```

The genes for TAP1 and DRb are separated by approximately 300 kb, and the gene for DQb lies in between TAP1 and DRb. All 424 clones were analyzed individually using the above primer pairs or in duplex reactions containing primers for both TAP1 and DRb. PCR analysis of the first 144 clones revealed 4 clones (18, 27, 76, and 101) that were positive for all three primer pairs. Analysis of the remaining 280 clones revealed 13 (#s 168, 176, 197, 244, 266, 296, 314, 335, 338, 349, 359, 365, 386,) that were positive for the TAP1 and DRb primers. To confirm the presence or absence of the DQb gene, the last set of clones are amplified using DQb primers, and analyzed by Southern blot for the presence of bands reactive to radio-labeled primers. ES cell clones positive for the three genes are expanded in culture for mounting in agarose blocks for PFGE analysis.

Structural Analysis of ES clones containing APP sequences

Figure 10:
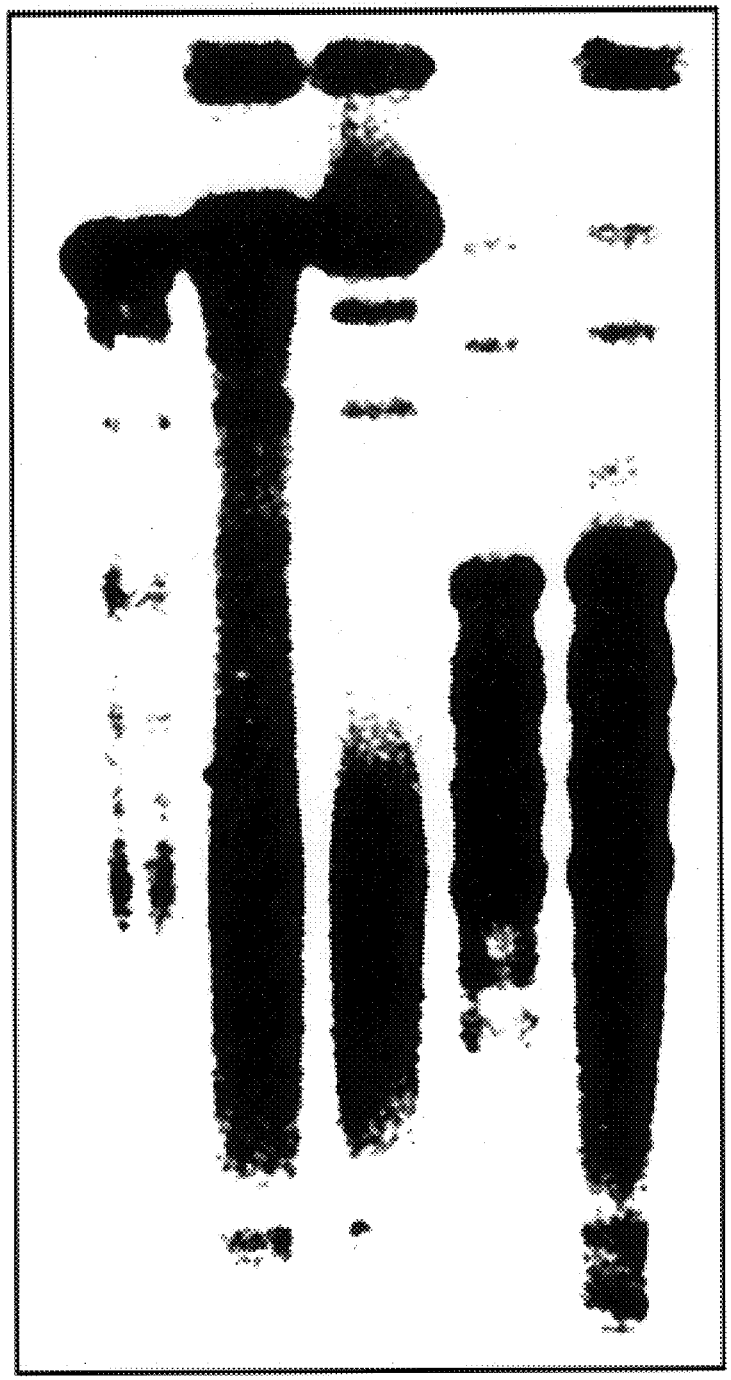
FIG. 10: SfiI fragments of human MHC class II YAC.

A physical map of the MHC Class II YAC is prepared as described in Example 2. Yeast DNA containing the 4D1 YAC is digested completely with rare cutter enzymes, such as Sfi I, Pac I, Swa I, Pme I and Apa I, and analyzed by PFGE Southern blotting using total human DNA as a probe for Alu fragments. The pattern of bands generated by Sfi I (FIG. 10) is used as a reference pattern since the size of the bands was well distributed between approximately 15 kb and 165 kb. The Sfi I pattern of human DNA fragments present in ES cell clones that received an intact YAC would be expected to resemble the pattern for 4D1 with the exception of the terminal fragments. The terminal fragments can be easily identified by reprobing the Sfi I digest with pBR322 sequences. The YAC can also be mapped by performing a partial Sfi I digest, as outlined in Example 2.

Individual ES cell lines are cultured and mounted in agarose blocks. The Sfi I restriction fragment pattern of PCR positive clones is analyzed and compared to that derived from the partental YAC clone. Those clones displaying a matched rare cutter fingerprint are selected to derive transgenic mice via ES cell injection into blastocysts as described in Example 2.

Mouse Models of Autoimmunity

Due to the strong correlation between particular MHC haplotypes and autoimmune disease in humans, there is a strong interest in determining how particular genes within the MHC locus contribute to disease. The human MHC locus contains the Class I and II genes, and expresses over 70 other genes. A number of these genes, such as those encoding the complement proteins, the cytokines tumor necrosis factor (TNF)-a and -b, and the TAP1/2 peptide transporters, play significant roles in the immune response. Expression of large regions of the human MHC locus in mice may therefore lead to the development of disease related phenotypes due to the interplay of multiple genetic factors. In particular, the Class II haplotype found on the YAC clone 4D1, above, is strongly correlated with coeliac disease (Lundin et al. (1993) J. Exp. Med. 178: 187–196) and type I diabetes, or insulin dependent diabetes mellitus (IDDM) (Campbell and Milner (1993) Curr. Opin. Immunol. 5: 887–893; Baisch et al. (1990) New England J. Med. 322: 1836–1841).

Although a number of human MHC genes associated with disease have been expressed in transgenic mice, they have not reproduced features of the human pathology. As disease models, the principle limitations of expressing particular Class I or Class II genes in mice appear to be (1) that the mouse may not provide the appropriate genetic background required to manifest the disease, and (2) the high probability that more than one gene is responsible for the disease. An example of the former is the fact that HLA B27 transgenic mice fail to show any signs of ankylosing spondylitis, whereas HLA B27 transgenic rats (Hammer et al. (1990) Cell 63: 1099–112) show remarkably similar signs of the human pathology. An example of the latter would be the mouse model for diabetes, the NOD mouse, which involves multiple genetic loci, including the MHC Class II region. Much controversy remains over the significance of genetic linkage between particular HLA haplotypes and the role of any given gene. Therefore the ability to introduce multi-gene loci via YAC transgenesis provides the opportunity to study the interplay of many disease factors, and may be coupled to the inactivation of endogenous mouse loci via homologous recombination strategies.

Mouse models of human immune cell function

An additional use of a human MHC Class II transgenic mouse is modeling the development and function of human lymphocytes. Engraftment of human immune cell progenitors or mature lymphocytes (e.g., peripheral blood lymphocytes, or PBLs) into immunodeficient mice provide relatively limited models of human immune cell differentiation or function. More appropriate systems include the ability of human cells to recognize and interact with human-specific adhesion molecules on the surface of the hosts cells . Mice expressing a repertoire of human lymphocyte adhesion molecules, including the Class I and Class II molecules, provide key elements for the normal differentiation and function of human lymphocytes. Thus, MHC Class II transgenic mice crossed with immunodeficient strains such as the severe combined immunodeficient (SCID) or recombination activation gene (RAG) mutant mice generate superior hosts for the engraftment of human immune cells.

Although the foregoing invention has been described in some detail by way of illustration and example, for purposes of clarity of understanding, it will be obvious that certain changes and modifications may be practiced within the scope of the appended claims.

We claim:

1. A method for producing a selectable co-lipofected mammalian cell having incorporated multiple heterologous DNA species, said mammalian cell having a genome comprising the steps of:

forming a co-lipofection complex comprising a cationic lipid, a first polynucleotide, said first polynucleotide being larger than 50 Kb, and an unlinked second polynucleotide comprising a selectable marker gene expression cassette;

contacting a mammalian cell with said co-lipofection complex under conditions whereby said first polynucleotide and said second polynucleotide are both introduced into said cell and are integrated into said genome to form a selectable co-lipofected mammalian cell having incorporated multiple heterologous DNA species.

2. A method according to claim 1, wherein said cationic lipid is selected from the group consisting of: N[1-(2,3-dioleoyloxyl)propyl]-N,N,N-trimethylammoniuim chloride; N[1-2,3-dioleoyloxyl)propyl]-N,N,N-trimethylammoniummethylsulfate; N-(2,3-di(9-(Z)-octadecenyloxy))-prop-1-N,N,N-trimethylammonium chloride; dioleoylphosphatidylethanolamine [(PtdEtn, DOPE)]; and dioctadeclyamidoglycyl spermidine.

3. A method according to claim 1, wherein the first polynucleotide is at least 500 kb.

4. A method according to claim 1, wherein said selectable marker is a drug resistance gene.

5. A method according to claim 4, wherein said selectable marker is a gene encoding neomycin resistance.

6. A method according to claim 1, further comprising the step of selecting for cells having said selectable marker.

7. A method according to claim 1, wherein said mammalian cell is a nonhuman embryonal stem cell.

8. A method according to claim 7, wherein said nonhuman embryonal stem cell is a mouse ES cell.

9. A method according to claim 8, wherein said cationic lipid is dioctadecylamidoglycyl spermidine (DOGS), said first polnucleotide contains a human genomic fragment containing an APP gene sequence, and said unlinked second polynucleotide contains a neomycin resistance gene.

10. A method according to claim 1, wherein said first polynucleotide comprises yeast-derived sequences.

11. The method of claim 1, wherein said first polynucleotide is less than 2000 Kb.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (primer)

(xi) SEQUENCE DESCRIPTION: SEQ ID NO:1:

GCTTTTGACG TTGGGGGTTA                                               20

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (primer)

(xi) SEQUENCE DESCRIPTION: SEQ ID NO:2:

TTCGTGAACA GTGGGAGGGA                                               20

(2) INFORMATION FOR SEQ ID NO:3:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (primer)

(xi) SEQUENCE DESCRIPTION: SEQ ID NO:3:

ATAACCTCAT CCAAATGTCC CC                                            22

(2) INFORMATION FOR SEQ ID NO:4:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (primer)

(xi) SEQUENCE DESCRIPTION: SEQ ID NO:4:

GTAACCCAAG CATCATGGAA GC                                            22

(2) INFORMATION FOR SEQ ID NO:5:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (oligonucleotide)

(xi) SEQUENCE DESCRIPTION: SEQ ID NO:5:

CAGGAATTCC ACCACAGAGT CTGTGGAA                                    28

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:6:

CAGGATCCGT GTCTCGAGAT ACTTGTCA                                     28

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:7:

CAGGAATTCC ACCACTGAGT CCGTGGAG                                     28

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:8:

CAGGATCCGT GTCTCCAGGT ACTTGTCG                                     28

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:9:

CAGGTACAGC TGCAGCAGTC A                                            21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:10:

TCCGGAGTCA CAGAGTTCAG C                                            21